(12) United States Patent
Tipping

(10) Patent No.: US 10,675,159 B2
(45) Date of Patent: Jun. 9, 2020

(54) COMPOSITE INTERBODY SYSTEM

(71) Applicant: Osseus Fusion Systems, LLC, Dallas, TX (US)

(72) Inventor: Chase D. Tipping, Dallas, TX (US)

(*) Notice: Subject to any disclaimer, the term of this patent is extended or adjusted under 35 U.S.C. 154(b) by 158 days.

(21) Appl. No.: 15/428,138

(22) Filed: Feb. 8, 2017

(65) Prior Publication Data
US 2019/0142600 A1    May 16, 2019

(51) Int. Cl.
*A61F 2/44* (2006.01)
*A61L 27/18* (2006.01)
*A61L 27/06* (2006.01)
*A61L 27/50* (2006.01)
*A61F 2/30* (2006.01)

(52) U.S. Cl.
CPC .............. *A61F 2/447* (2013.01); *A61L 27/06* (2013.01); *A61L 27/18* (2013.01); *A61L 27/50* (2013.01); *A61F 2002/30028* (2013.01); *A61F 2002/3093* (2013.01); *A61F 2002/30331* (2013.01); *A61F 2002/30354* (2013.01); *A61F 2002/30403* (2013.01); *A61F 2002/30433* (2013.01); *A61F 2002/30593* (2013.01); *A61F 2002/30604* (2013.01); *A61F 2002/30622* (2013.01); *A61F 2002/30785* (2013.01); *A61F 2002/30789* (2013.01); *A61F 2310/00023* (2013.01); *A61L 2430/02* (2013.01); *A61L 2430/38* (2013.01)

(58) Field of Classification Search
CPC .. A61F 2/44; A61F 2/447; A61F 2002/30029; A61F 2002/30354; A61F 2002/3038; A61F 2002/30403; A61F 2002/30433; A61F 2002/30604; A61F 2002/30622; A61F 2002/30785; A61F 2002/30789; A61F 2002/3093; A61F 2002/4475; A61F 2002/38; A61F 2002/30387–30389; A61F 2002/304–30403; A61L 27/06; A61L 27/18; A61L 2430/02
USPC ............................................ 623/17.11–17.16
See application file for complete search history.

(56) References Cited

U.S. PATENT DOCUMENTS

| | | | | |
|---|---|---|---|---|
| 5,171,281 A * | 12/1992 | Parsons | ................... | A61F 2/442 623/17.15 |
| 6,569,201 B2 * | 5/2003 | Moumene | ............... | A61F 2/447 606/247 |
| 7,776,093 B2 * | 8/2010 | Wolek | ....................... | A61F 2/44 623/17.16 |
| 2003/0187506 A1 * | 10/2003 | Ross | ....................... | A61F 2/442 623/17.13 |
| 2008/0154379 A1 * | 6/2008 | Steiner | .................. | A61F 2/4455 623/17.16 |
| 2010/0094426 A1 * | 4/2010 | Grohowski, Jr. | ........ | A61F 2/447 623/17.16 |
| 2011/0190888 A1 * | 8/2011 | Bertele | ............... | A61F 2/30907 623/17.11 |

(Continued)

*Primary Examiner* — Jessica Weiss
(74) *Attorney, Agent, or Firm* — Merle W Richman, Esq.

(57) ABSTRACT

Embodiments of a composite interbody system 10 for treating mammalian bony segments including various materials to encourage bony fusion while enabling radiographic visualization where the composite interbody system 10 may be employed between two, adjacent mammalian bony segments to stabilize, maintain spacing between, or couple the bony segments. Other embodiments may be described and claimed.

14 Claims, 25 Drawing Sheets

(56) References Cited

U.S. PATENT DOCUMENTS

| | | | |
|---|---|---|---|
| 2012/0303128 A1* | 11/2012 | Ullrich, Jr. | A61F 2/4465 623/17.16 |
| 2013/0073046 A1* | 3/2013 | Zaveloff | A61F 2/442 623/17.16 |
| 2013/0085573 A1* | 4/2013 | Lemoine | A61F 2/4465 623/17.16 |
| 2013/0110243 A1* | 5/2013 | Patterson et al. | A61F 2/44 623/17.16 |
| 2014/0257492 A1* | 9/2014 | Schwab | A61F 2/4465 623/17.16 |
| 2014/0277482 A1* | 9/2014 | Gfeller | B29C 45/14467 623/17.16 |
| 2014/0277491 A1* | 9/2014 | Fang | A61F 2/447 623/17.16 |
| 2016/0128843 A1* | 5/2016 | Tsau | A61L 27/50 623/17.16 |

\* cited by examiner

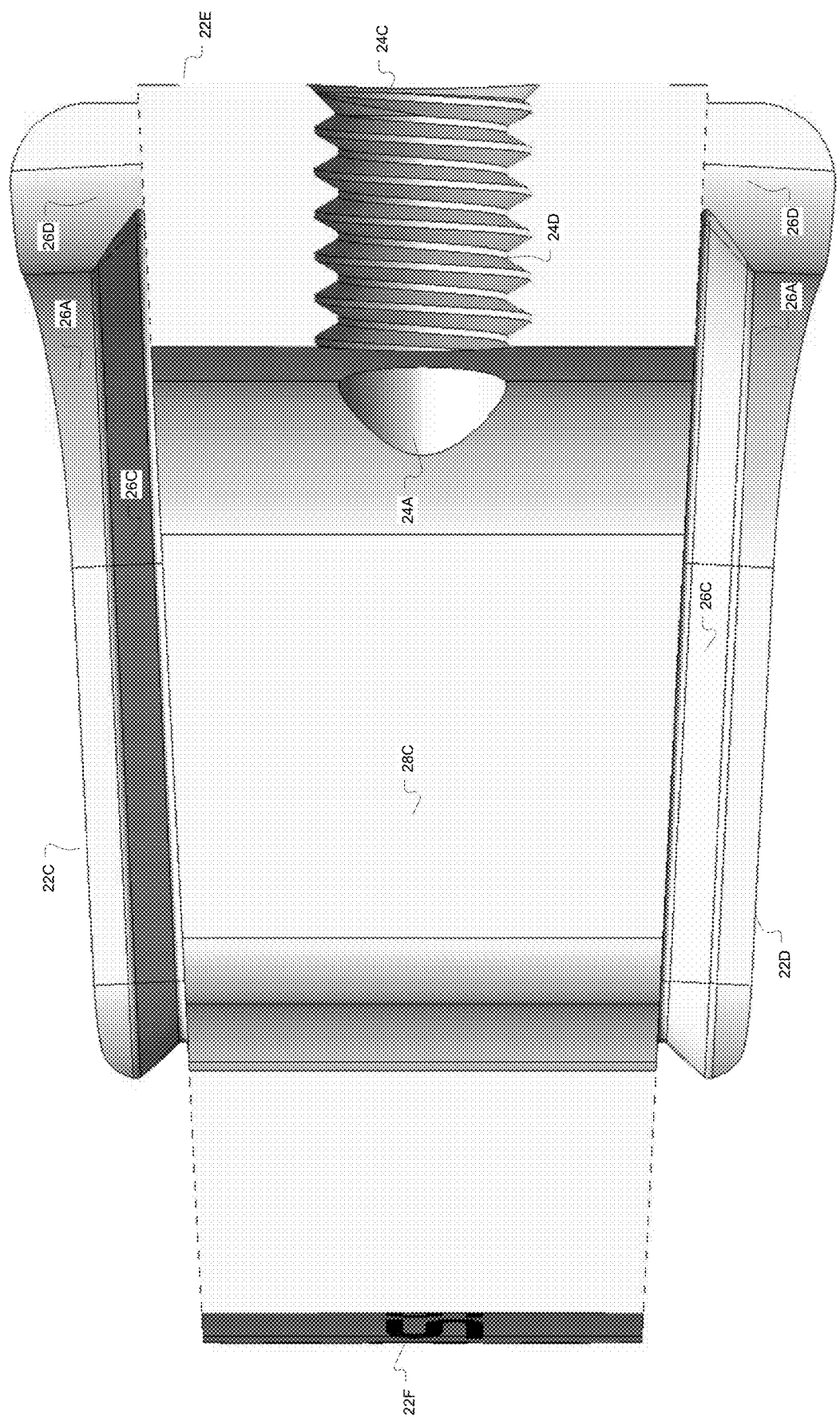

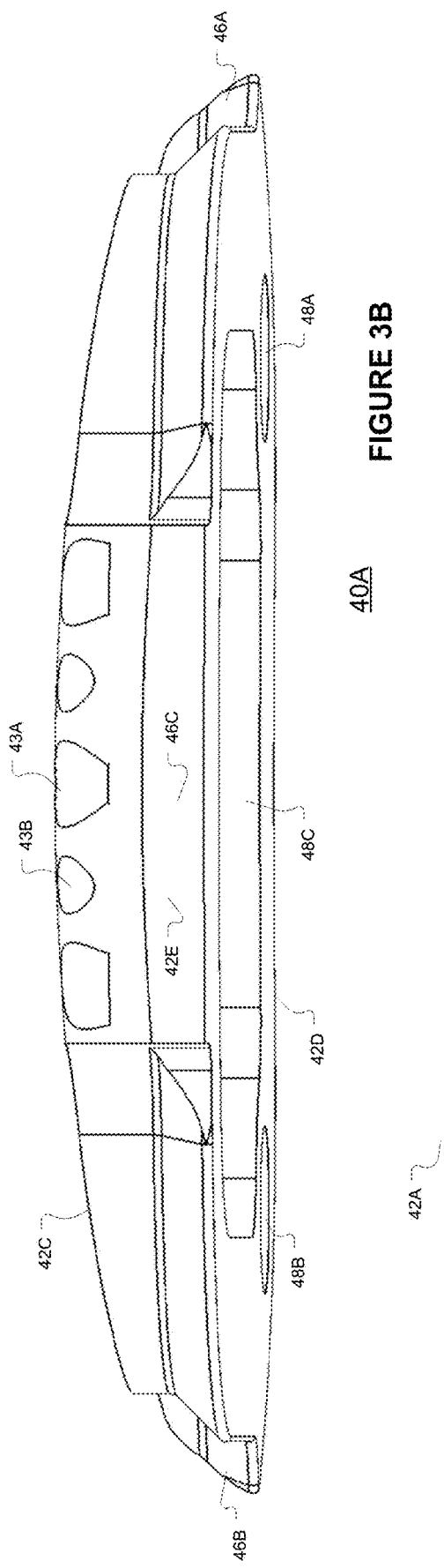

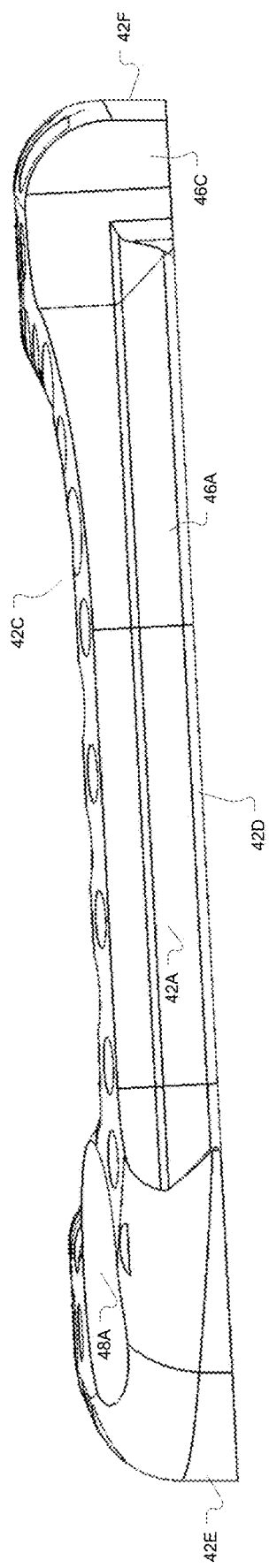
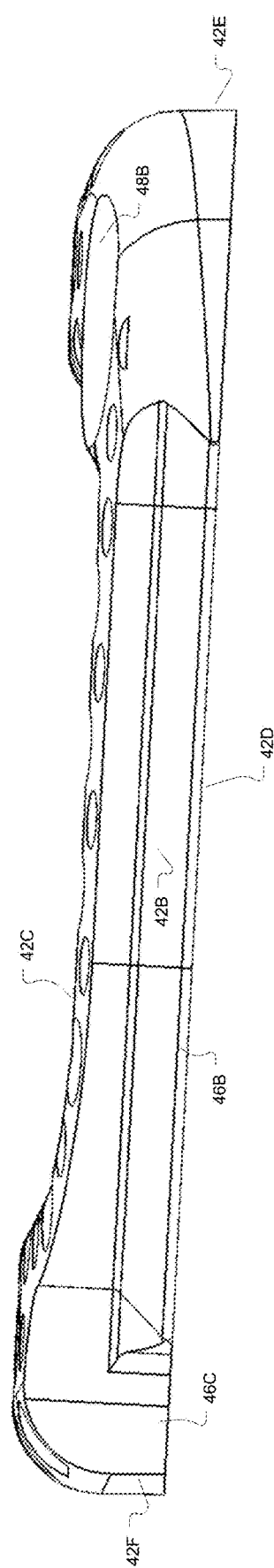

COMPOSITE INTERBODY SYSTEM

TECHNICAL FIELD

Various embodiments described herein relate generally to treating mammalian bony segments, including systems and methods that employ an interbody implant to stabilize, maintain spacing between, or couple one or more mammalian bony segments.

BACKGROUND INFORMATION

It may be desirable to treat one or more bony segments via an interbody implant that enables visualization while enabling bony fusion, providing stabilization, or maintaining a desired spacing between bony segments, the present invention provides such an interbody implant.

BRIEF DESCRIPTION OF THE DRAWINGS

FIG. 2B is a simplified vertical cross sectional left side view of the main module of a composite interbody system shown in FIG. 2C taken along line CC according to various embodiments.

FIG. 3B is a simplified front view of an upper module of a composite interbody system according to various embodiments.

FIG. 3C is a simplified rear view of an upper module of a composite interbody system according to various embodiments.

FIG. 3F is a simplified right side view of an upper module of a composite interbody system according to various embodiments.

FIG. 3G is a simplified left side view of an upper module of a composite interbody system according to various embodiments.

DETAILED DESCRIPTION

Figure 5B:
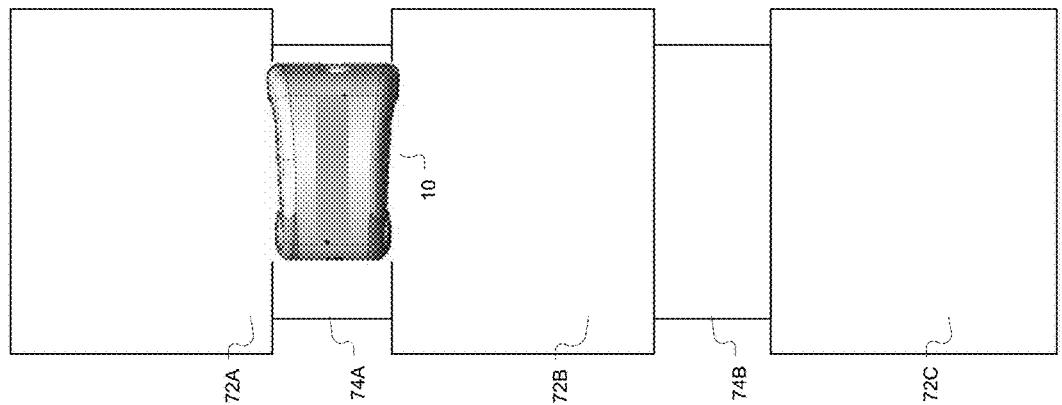
FIG. 5B is a left side view of a body segment treatment architecture including a composite interbody system operatively between a center bony segment and an adjacent upper bony segment according to various embodiments.
Figure 5A:
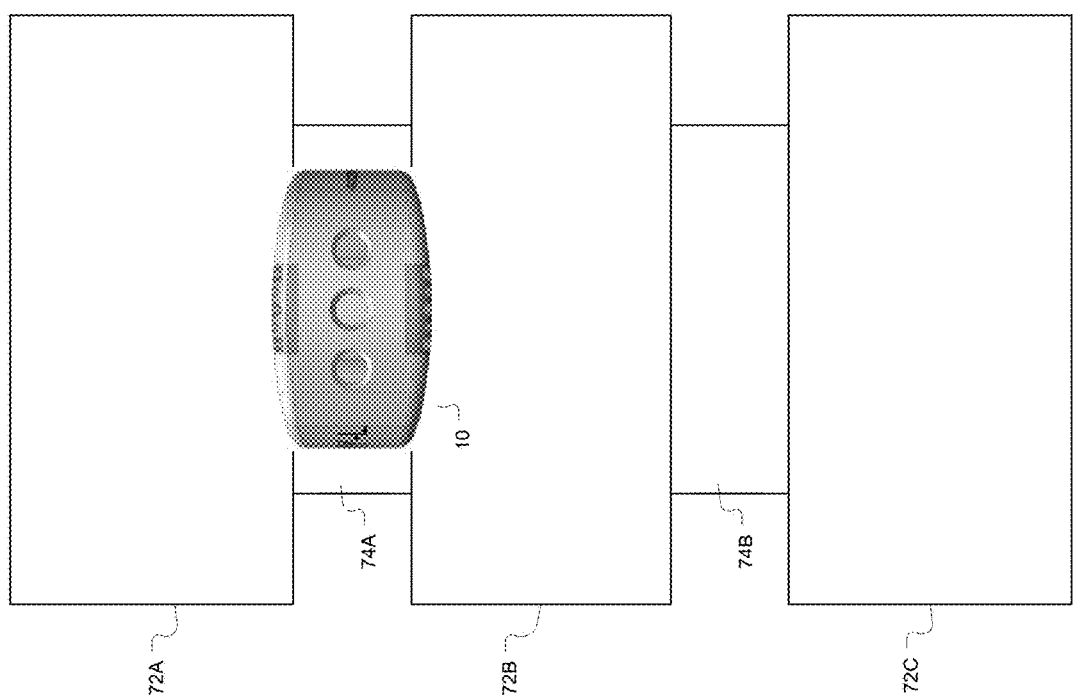
FIG. 5A is a posterior view of a body segment treatment architecture including a composite interbody system operatively between a center bony segment and an adjacent upper bony segment according to various embodiments.

It may be desirable to place an interbody implant 10 between two, adjacent bony regions or segments 72A-C as shown in architecture 70 in FIGS. 5A-5B to enable the regions to become stabilized, joined, separated by a minimum distance, or fused together. The bony segments 72A-C may be separated by one or more non-bony elements 74A-B, for example the bony segments 72A-C may be vertebra separated by spinal discs 74A-B in a cervical, thoracic, or lumbar region of a mammal including a human.

In an embodiment, an interbody implant 10 may be inserted between adjacent bony segments 72A-C in order to maintain a desired distance between the segments 72A-C. After insertion, an interbody implant 10 may ideally fuse with the adjacent segments 72A-C to form a bony fusion between the segments 72A-C while maintaining the desired distance between the segments 72A-C. In addition, a medical professional may wish to verify the implant's location between the segments 72A-C via a radiation based imaging system. The interbody implant 10 according to an embodiment is a composite interbody implant 10 including upper and lower modules 40A, 40B that promote bony fusion and a main module 20 that is substantially radiographically translucent.

Figure 1A:
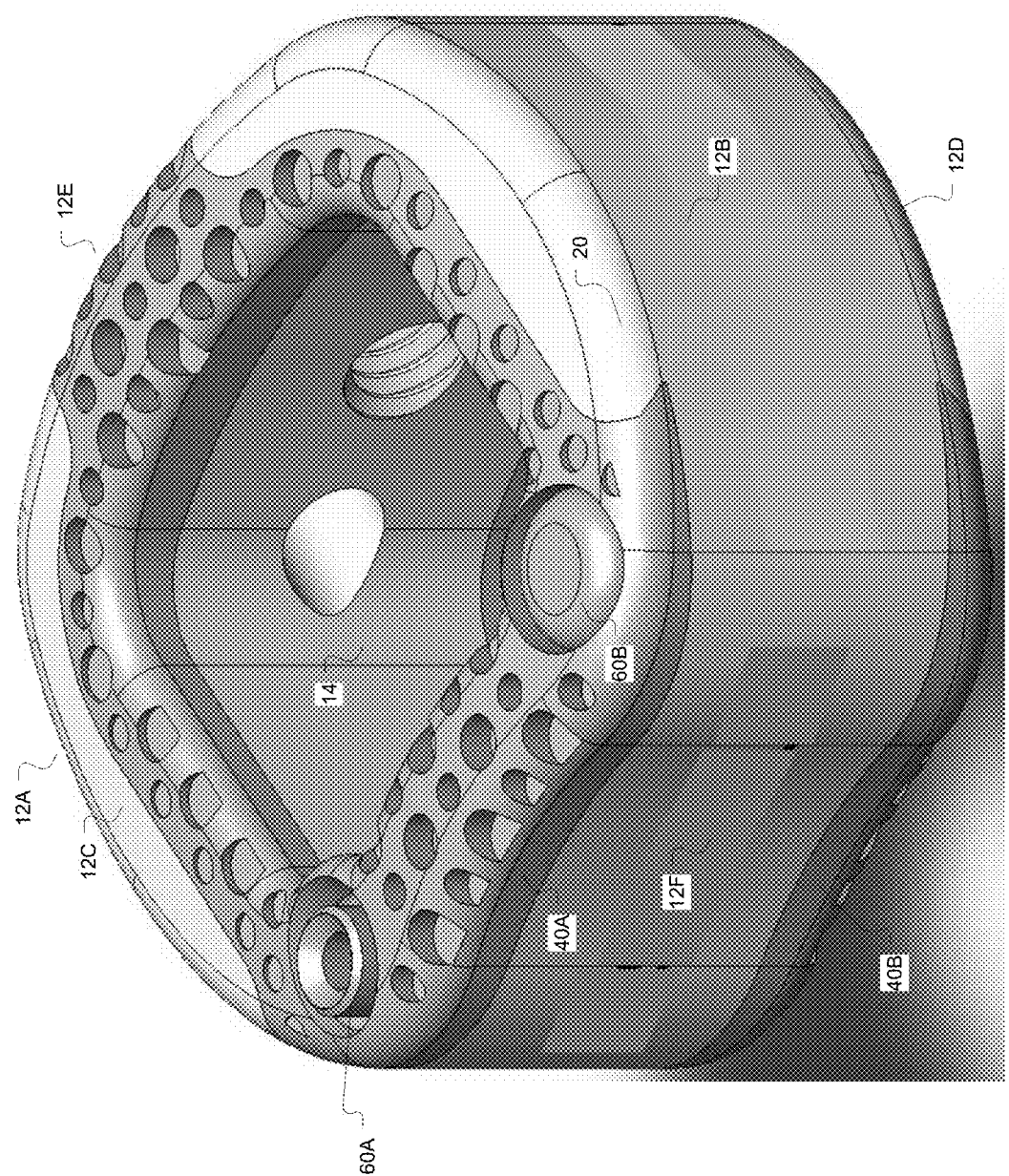
FIG. 1A is a simplified isometric view of a composite interbody system according to various embodiments.

FIG. 1A is a simplified isometric view of a composite interbody system 10 according to various embodiments. As shown in FIG. 1A, the composite interbody system 10 may include a main module 20, an upper module 40A, a lower module 40B, a first linking module 60A, and a second linking module 60B. As shown in FIG. 1A, the composite interbody system 10 may be substantially cubic in shape with convexly curved right, left, and front sides 12A, 12B, 12E, a concavely curved back side 12F, and a large central fenestration 14 extending from a top side 12C to a bottom side 12D of the system 10.

Figure 1B:
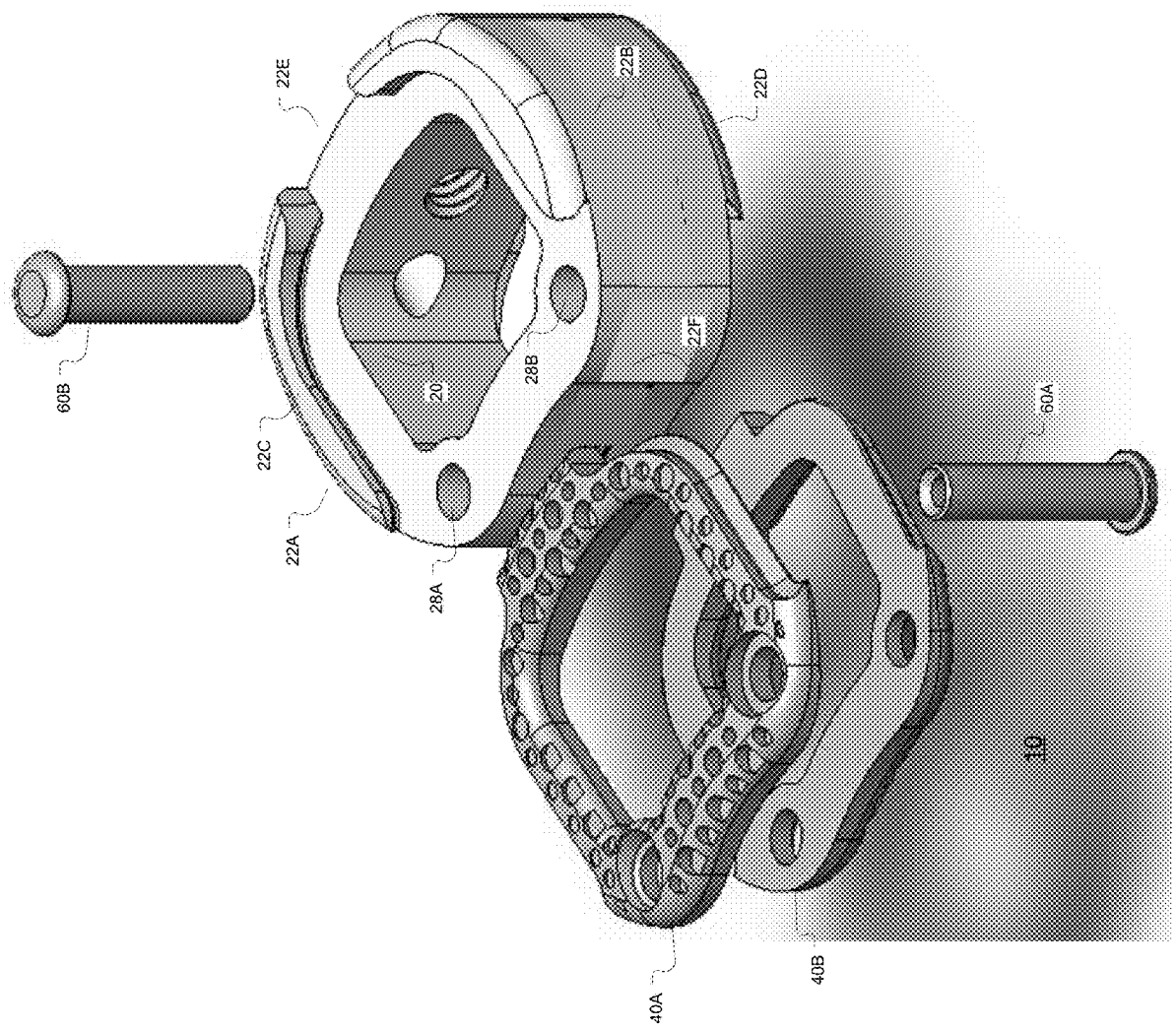
FIG. 1B is a simplified isometric, exploded view of a composite interbody system according to various embodiments.

FIG. 1B is a simplified isometric, exploded view of the composite interbody system 10 according to various embodiments. As shown in FIG. 1B, in an embodiment, the upper module 40A may be slidably coupled to front 22E and side 22A, 22B portions of the top side 22C of the main module 20. The lower module 40B may be similarly slidably coupled to front 22E and side 22A, 22B portions of the bottom side 22C of the main module 20. The upper module 40A may be fixably coupled to back 22F portions of the top side 22C of the main module 20 and the lower module 40B may be fixably coupled to back 22F portions of the bottom side 22D of the main module 20 via a right linking module 60A and a left linking module 60B. In an embodiment, the right linking module 60A may fixably link the upper module 40A to the lower module 40B via the main module 20 right, back fenestration 28A. Similarly, the left linking module 60B may fixably link the upper module 40A to the lower module 40B via the main module 20 left, back fenestration 28B.

In an embodiment, the main module 20 is formed of a first material or complex of materials. The upper and lower modules 40A, 40B may be formed of a second, different material or complex of materials. In an embodiment, the upper and lower modules 40A, 40B may be formed of different materials or complex of materials. In an embodiment, the right and left linking modules 60A, 60B may be formed of a third, different material or complex of materials. In an embodiment, the right and left linking modules 60A, 60B may be formed of a different materials or complex of materials. In an additional embodiment, the upper and lower modules 40A, 40B and the right and left linking modules 60A, 60B may be formed of the same second material or complex of materials.

In an embodiment, the first material or complex of materials may be a biocompatible, substantially radio-lucent material or complex of materials. In an embodiment, the first material or complex of materials may be a biocompatible, radio-opaque material or complex of materials. In an embodiment, the second material or complex of materials may be a biocompatible, substantially radio-opaque material or complex of materials. In an embodiment, the third material or complex of materials may be a biocompatible, substantially radio-opaque material or complex of materials.

In an embodiment, the second material or complex of materials may be a biocompatible, osteoconductive material or complex of materials. In an embodiment, the third material or complex of materials may also be a biocompatible, osteoconductive material or complex of materials. In an embodiment, the first material or complex of materials may also be a biocompatible, less osteoconductive material or complex of materials than the first and second materials or complex of materials. In an embodiment, the main module 20 may be formed of a polymer, ceramic, or combination of both, including Polyether ether ketone (PEEK) or other member of the polyaryletherketone family. The upper and lower modules 40A, 40B may be formed of a metal, alloy, or other osteoconductive material. In an embodiment, the upper and lower modules 40A, 40B may be formed from Titanium. The right and left linking modules 60A, 60B may be formed of a metal, alloy, or other biocompatible material. In an embodiment, the right and left linking modules 60A, 60B may be formed from Titanium.

In an embodiment, a composite interbody system 10 may be employed between cervical vertebrae in a human. For such an application or use, a composite interbody system 10 may have a maximum length (from front side 12E to back side 12F) of about 6 to 18 mm and 12 mm in an embodiment where the maximum length may vary as function of its intended use or placement. A composite interbody system 10 may have a maximum width (from right side 12A to left side 12B) of about 6 to 20 mm and 14 mm in an embodiment where the maximum width may also vary as function of its intended use or placement. A composite interbody system 10 may have a maximum height (from top side 12C to bottom side 12D) of about 3 to 18 mm and 5 mm to 12 mm in an embodiment where the maximum height may also vary as function of its intended use or placement and the desired minimum distance between bony segments 72A-C. In an embodiment, a composite interbody system 10 central fenestration 14 opening maximum length (from front to back) may be about 3 to 15 mm and 7 mm in an embodiment where the maximum length may vary as function of its intended use or placement. A composite interbody system 10 may have a maximum width (from right side 12A to left side 12B) of about 3 to 15 mm and 8 mm in an embodiment where the maximum width may also vary as function of its intended use or placement.

Figure 1C:
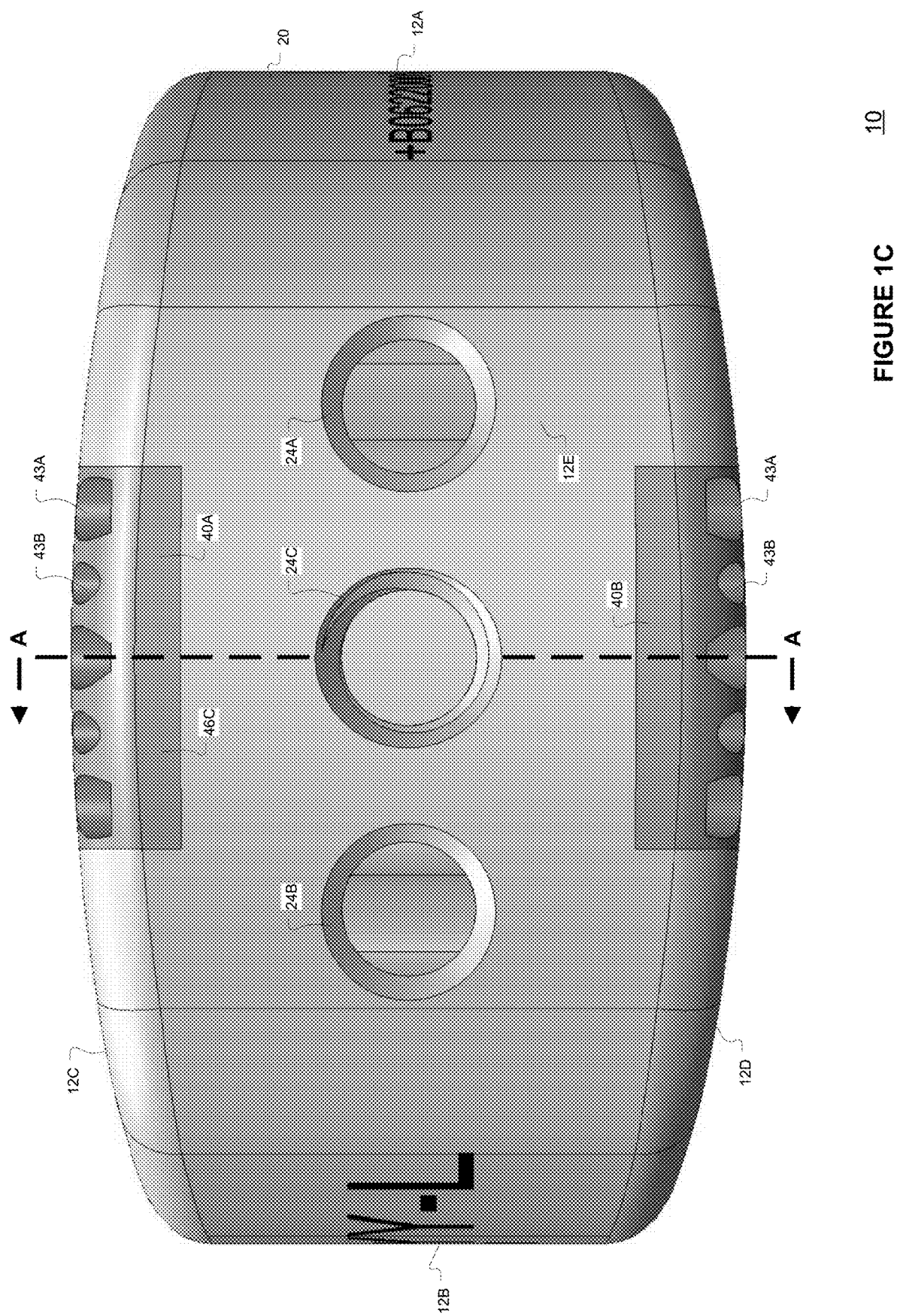
FIG. 1C is a simplified front view of a composite interbody system according to various embodiments.

FIG. 1C is a simplified front view of a composite interbody system 10 according to various embodiments. As shown in FIG. 1C, the composite interbody system 10 front side 12E may include several penetrations 24A, 24B, 24C. In an embodiment, the penetrations 24A-24C may extend front side 12E to the central vertical fenestration 14 and form front side fenestrations. In an embodiment, the center fenestration 24C may be threaded to mate with a tool threaded pin. In a further embodiment, one or more of the other penetrations or fenestrations 24A, 24B may also be threaded. The combination of a threaded center fenestration 24C and the right and left fenestrations 24A, 24B may enable a medical professional to securely engage and rotate the composite interbody system 10 during implantation between two bony segments 72A-C or removal of the composite interbody system 10 (such as during a revision procedure). In an embodiment, the composite interbody system 10 is inserted between bony segments 72A-C starting with its back side 12F. In an embodiment, the fenestrations 24A-C may have a similar diameter of about 0.5 to 5 mm and 1.6 mm in an embodiment such a cervical spine application. The center fenestration 24C may be located about center (from top 12C to bottom 12D and left 12B to right 12A). The other fenestrations 24A, 24B may located centrally from the top 12C to bottom 12D and have a center about 1 mm to 6 mm from the fenestration 24C and about 3 mm in an embodiment.

Figure 2A:
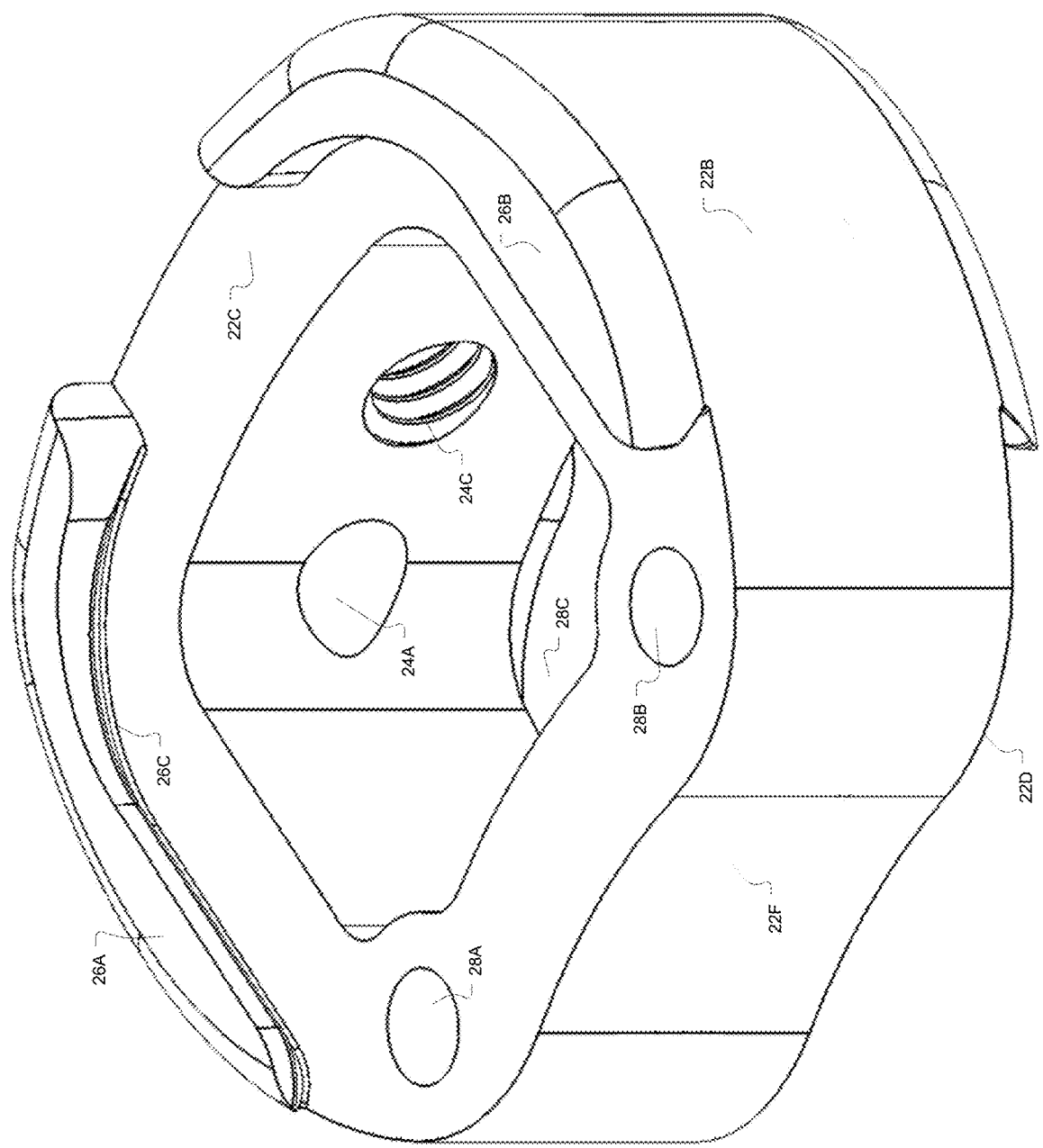
FIG. 2A is a simplified isometric view of a main module of a composite interbody system according to various embodiments.

As shown in FIG. 1C, the composite interbody system 10 top side 12C and bottom side 12D may be convexly curved from the approximate center of the front side 12E. In an embodiment, the effective curvature of the top side 12C and bottom side 12D measured from its peak (left and right of peak) is about 15 mm to 50 mm and about 30 mm in an embodiment. As shown in 1C, the upper and lower module 40A, 40B may have a front extension 46C that is sized to be placed between right and left shoulders 26A, 26B (FIG. 2A)

of the main module 20. It is noted that is an embodiment that the upper and lower modules 40A, 40B may be identical and the main module top side 22C layout and bottom side 22D layout may also be identical.

Figure 1D:
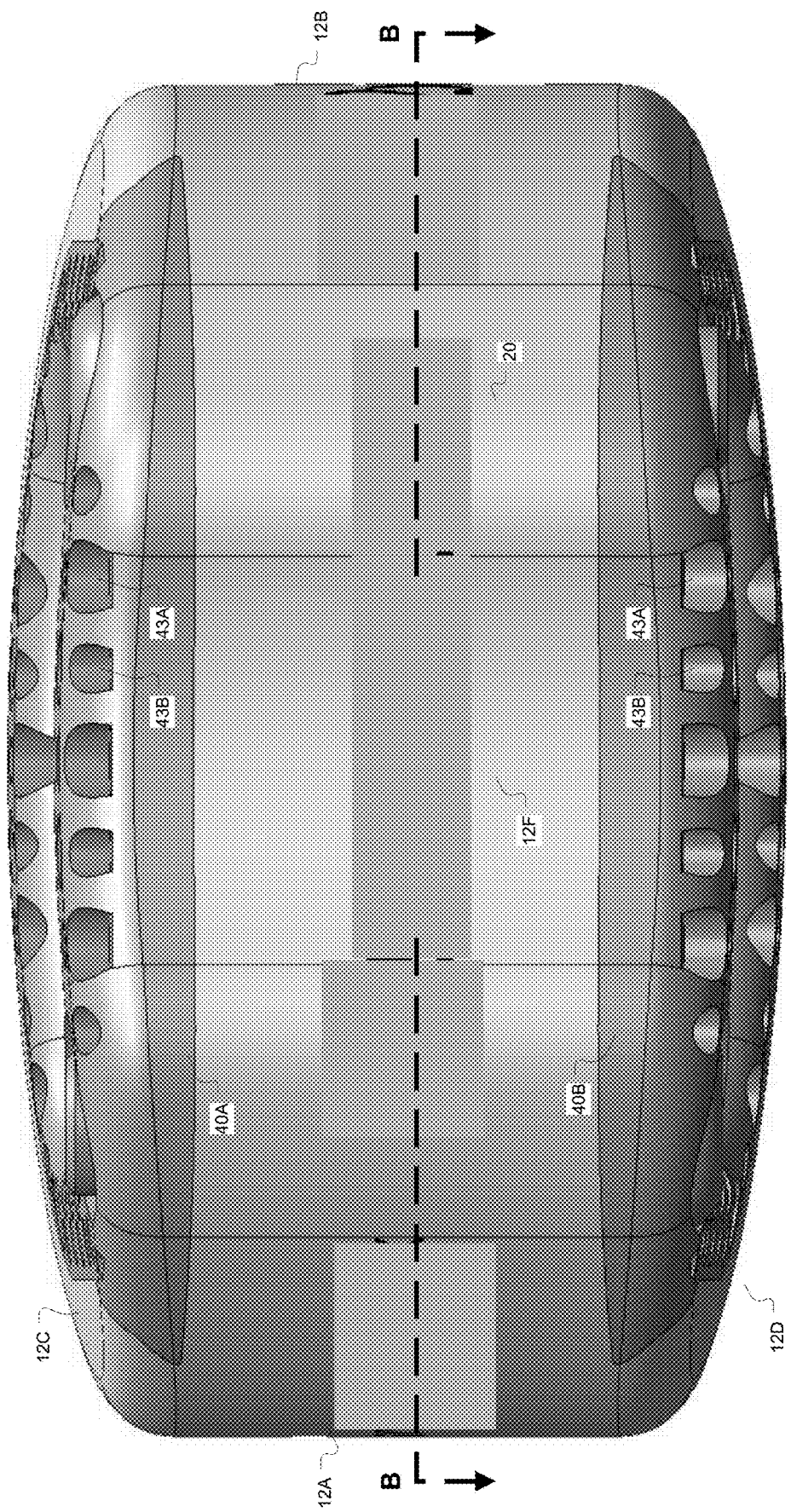
FIG. 1D is a simplified rear view of a composite interbody system according to various embodiments.
Figure 1E:
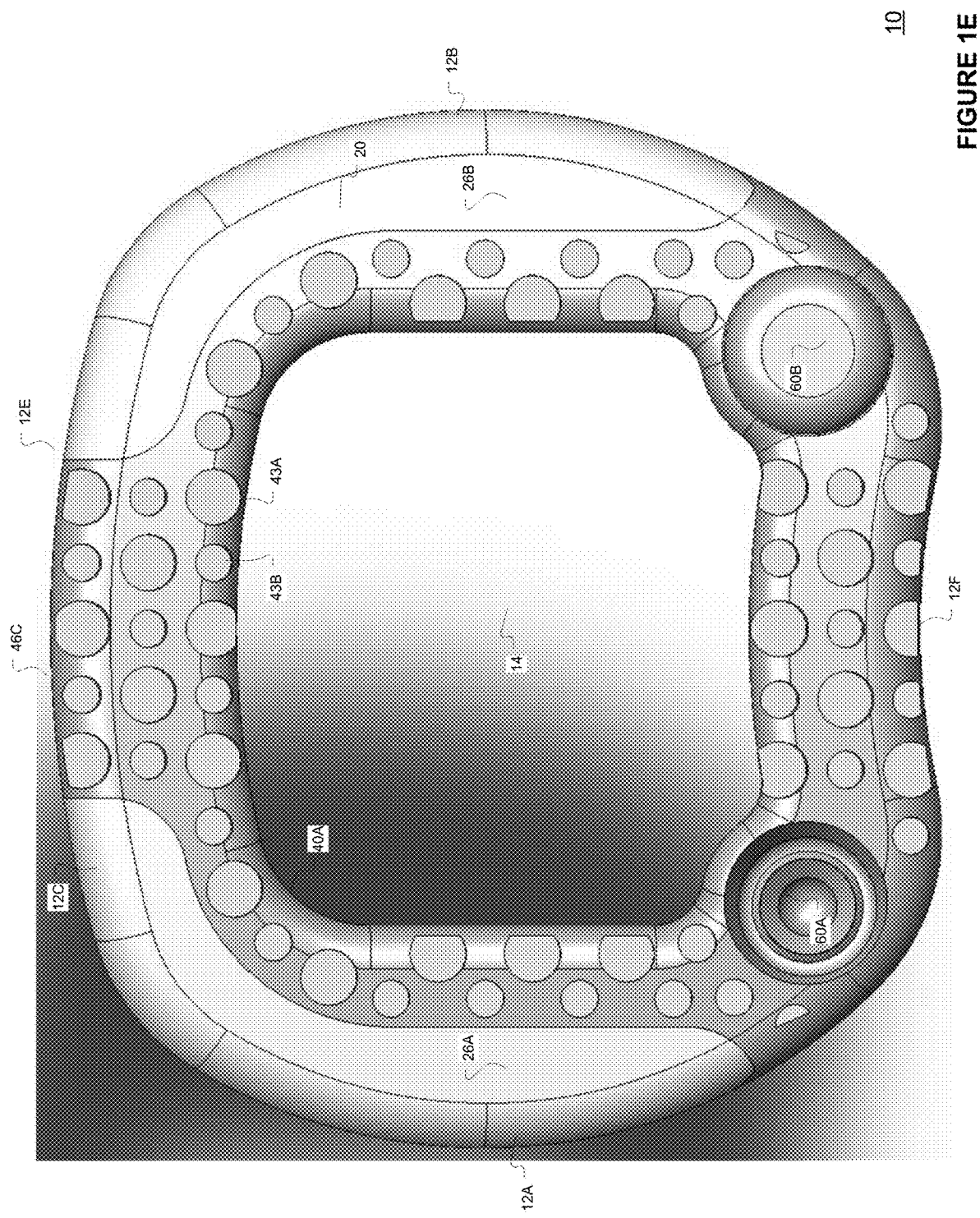
FIG. 1E is a simplified top view of a composite interbody system according to various embodiments.

FIG. 1D is a simplified rear view of a composite interbody system 10 according to various embodiments. As shown in FIGS. 1A, 1B, and 1D (and others), the composite interbody system 10 is sloped from its front side 12E to its back side 12F. In an embodiment, the composite interbody system 10 may be sloped about 2 to 12 degrees from its front side 12E to back side 12F as function of its intended application and about 6 degrees for a cervical spine application in an embodiment. FIG. 1E is a simplified top view of a composite interbody system 10 according to various embodiments. As shown in FIG. 1E, the composite interbody system 10 main module 20 may has partial shoulders 26A, 26B where the upper module 40A is inset on the right side 12A and left side 12B and extends to the front 12E and back area 12F. The upper and lower modules 40A, 40B may be effectively plates in an embodiment and have fenestration that matches the composite interbody system 10 fenestration 14 and the main body fenestration 28C. In an embodiment, the composite interbody system 10 right 12A and left 12B wall maximum thickness may be about 1 to 5 mm and about 3 mm in an embodiment. In an embodiment, the composite interbody system 10 front 12E and back 12F wall maximum thickness may be about 1 to 5 mm and about 2.5 mm in an embodiment.

Figure 1F:
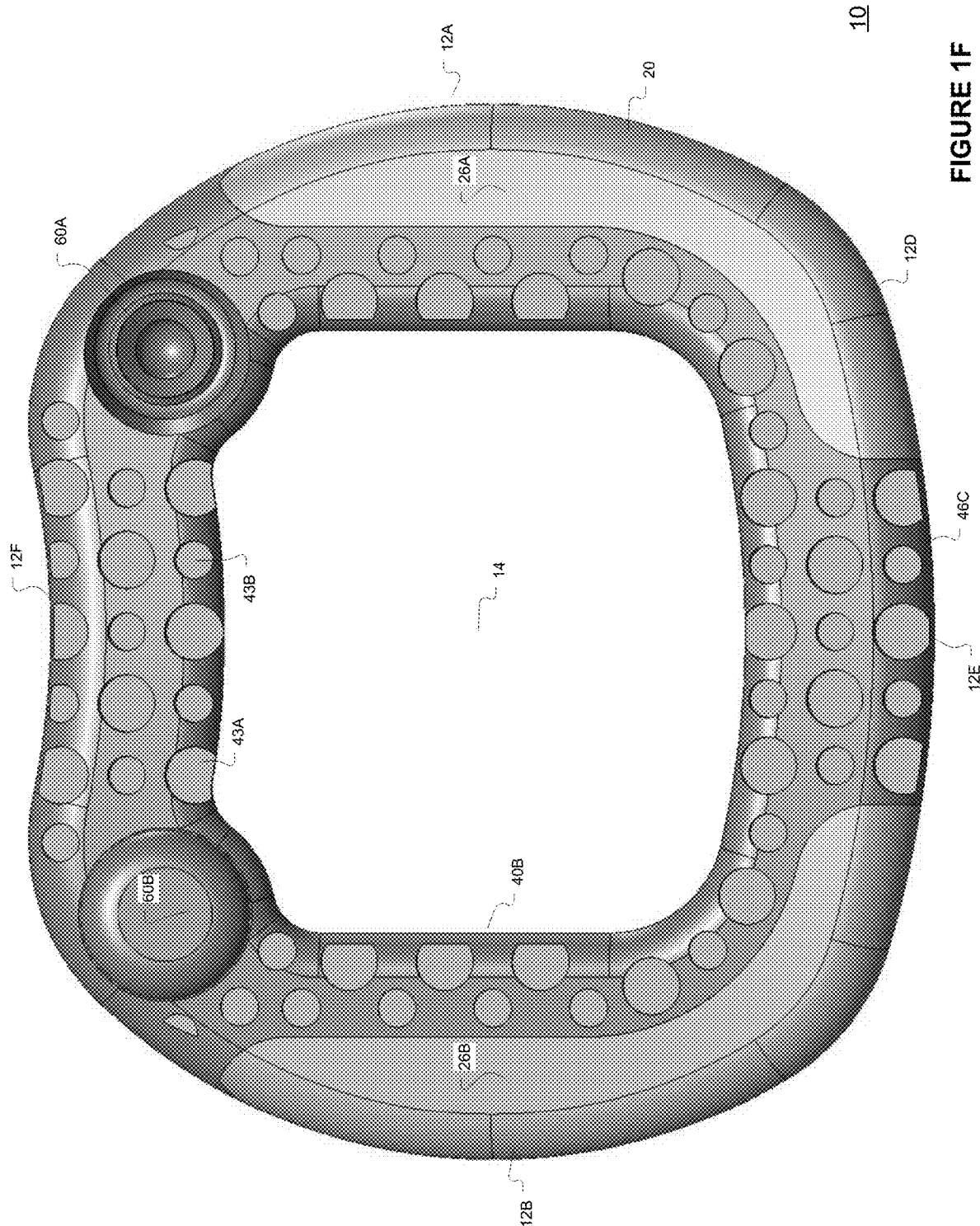
FIG. 1F is a simplified bottom view of a composite interbody system according to various embodiments.

As shown in FIGS. 1E and 1F, a substantial portion of composite interbody system 10 top 12C surface area and bottom 12D surface area is provided by the upper and lower modules 40A, 40B. As noted the upper and lower modules 40A, 40B may be comprised of an osteoconductive material and may be positioned in a cervical spine application to engage cancellous bone, thereby increasing the possibility of bony fusion with adjacent segments or vertebrae 72A-C. Further, as show in FIGS. 1A-1J and 3A-3C, the upper and lower modules 40A, 40B may include various sized divots 43A, 43B that may further induce bony in growths and thus bony fusion. In an embodiment, the divots or holes 43A, 43B may have a diameter of about 0.2 to 2 mm and about 0.75 mm and 0.5 mm respectively. The divots or holes 43A, 43B may have a depth of about 0.2 to 2 mm and about 0.5 mm respectively in an embodiment.

Figure 1G:
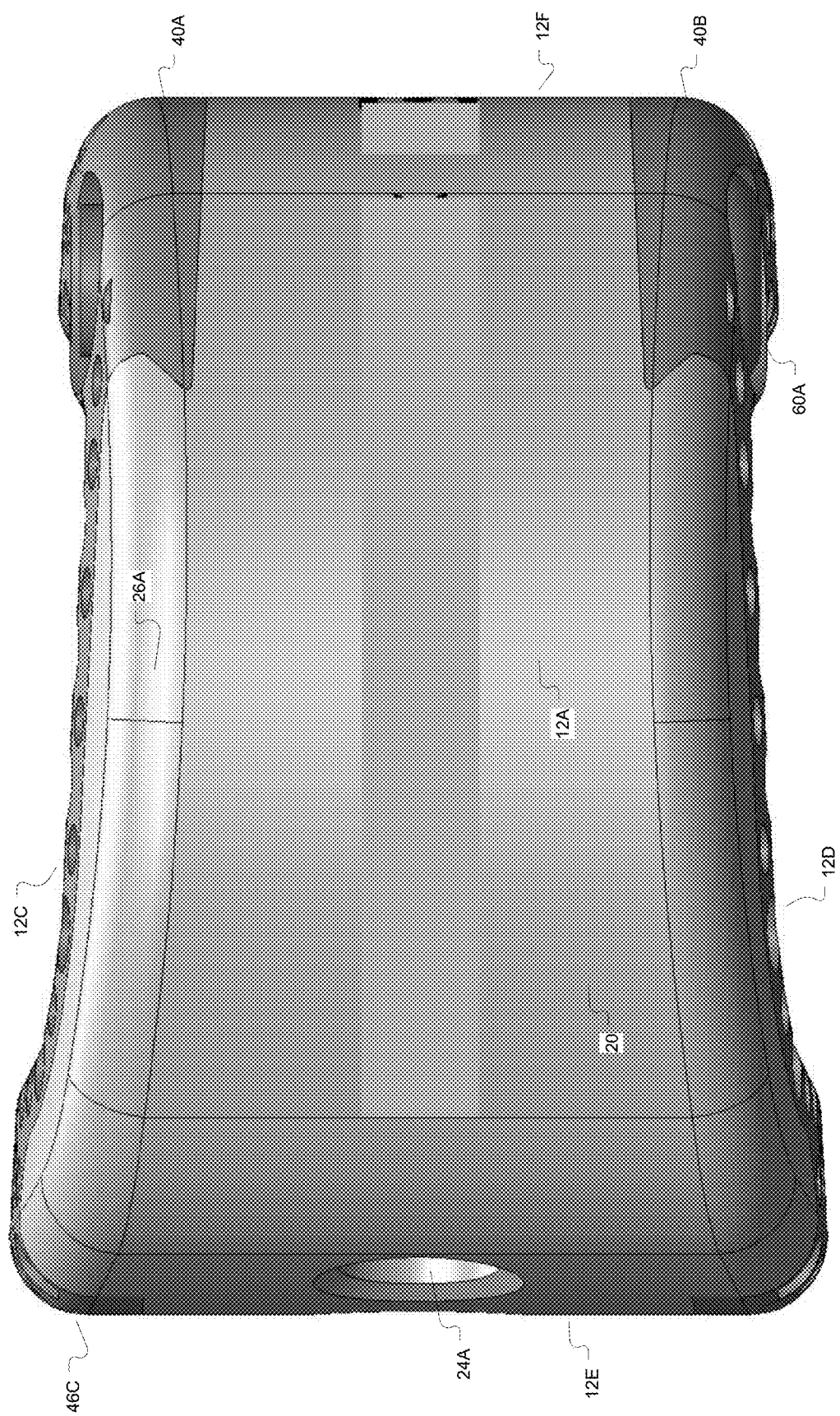
FIG. 1G is a simplified right side view of a composite interbody system according to various embodiments.
Figure 1H:
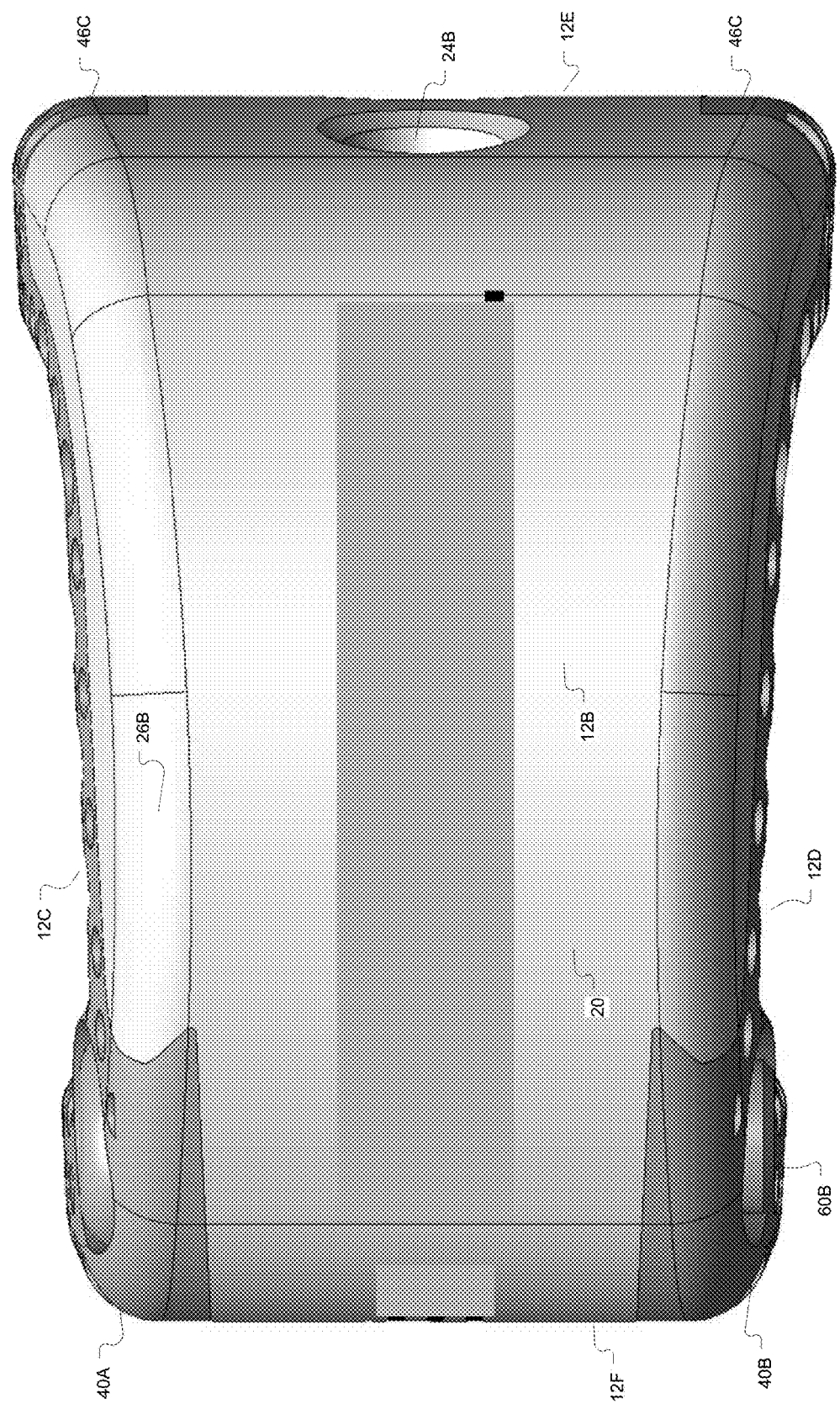
FIG. 1H is a simplified left side view of a composite interbody system according to various embodiments.

FIG. 1F is a simplified bottom view of a composite interbody system 10 according to various embodiments. As shown in FIG. 1F, the composite interbody system 10 bottom side 12D may be symmetrical to the composite interbody system 10 top side 12C. FIG. 1G is a simplified right side 12A view of a composite interbody system according to various embodiments. FIG. 1H is a simplified left side view 12B of a composite interbody system according to various embodiments. As shown in FIGS. 1G and 1H, the composite interbody system 10 right side 12A may be symmetrical to the composite interbody system 10 left side 12B. FIGS. 1G and 1H also shown how a portion the upper and lower modules 40A dovetails into the main module 20 shoulders 26A, 26B. The main module 20 shoulders 26A, 26B undercuts 26C enable the upper and lower modules 40A and 40B to slidably dovetail into the main body and secure the modules 40A, 40B right and left sides 42A, 42B to the main module 20. The linking modules 60A (right) and 60B (left) extending through the main body via fenestrations 28A, 28B and coupled to the modules 40A, 40B back 42F corners ensure the modules 40A, 40B do not slide relative to the main module 20.

Figure 1I:
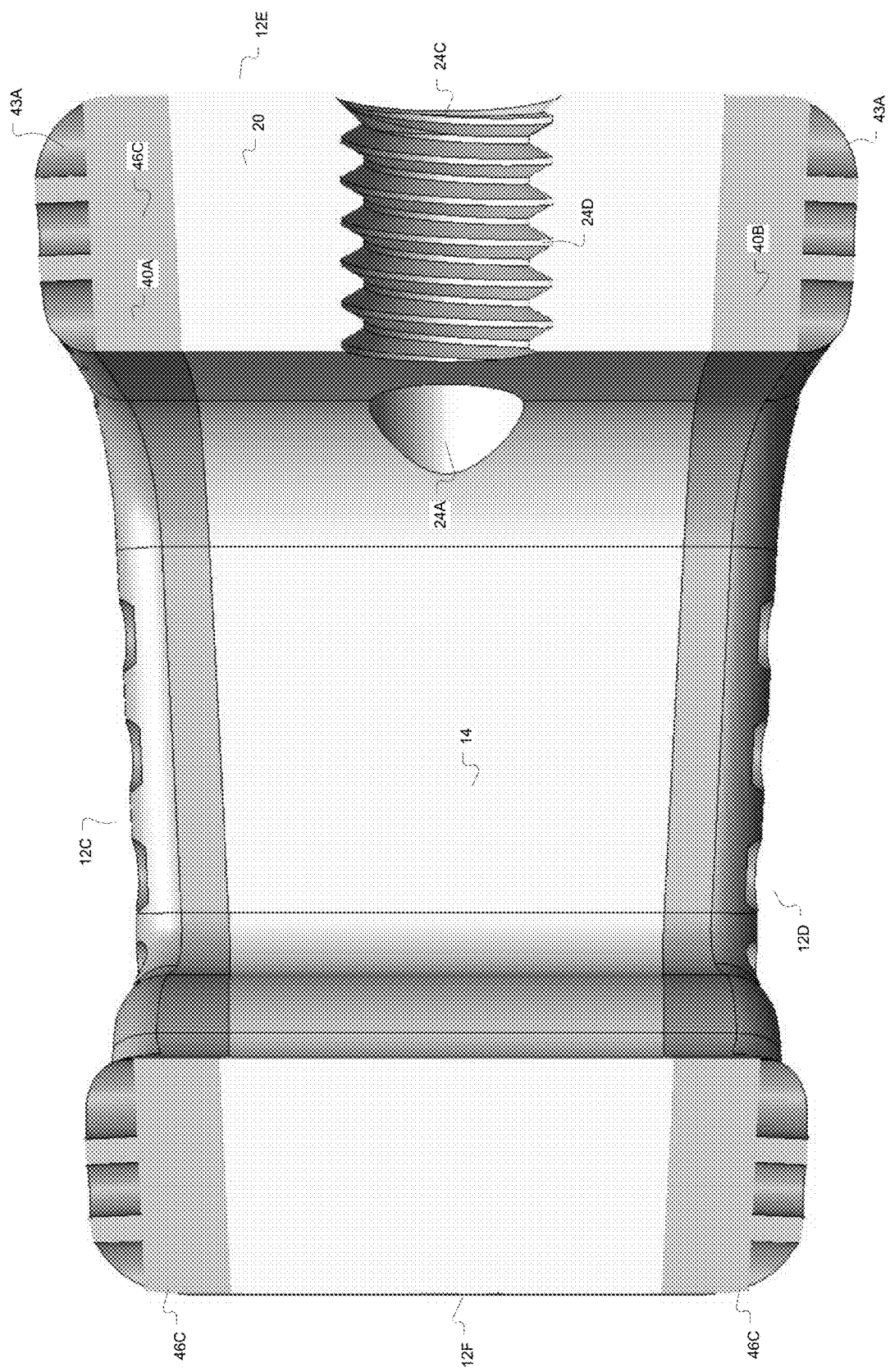
FIG. 1I is a simplified vertical cross sectional left side view of the composite interbody system shown in FIG. 1C taken along line AA according to various embodiments.
Figure 1J:
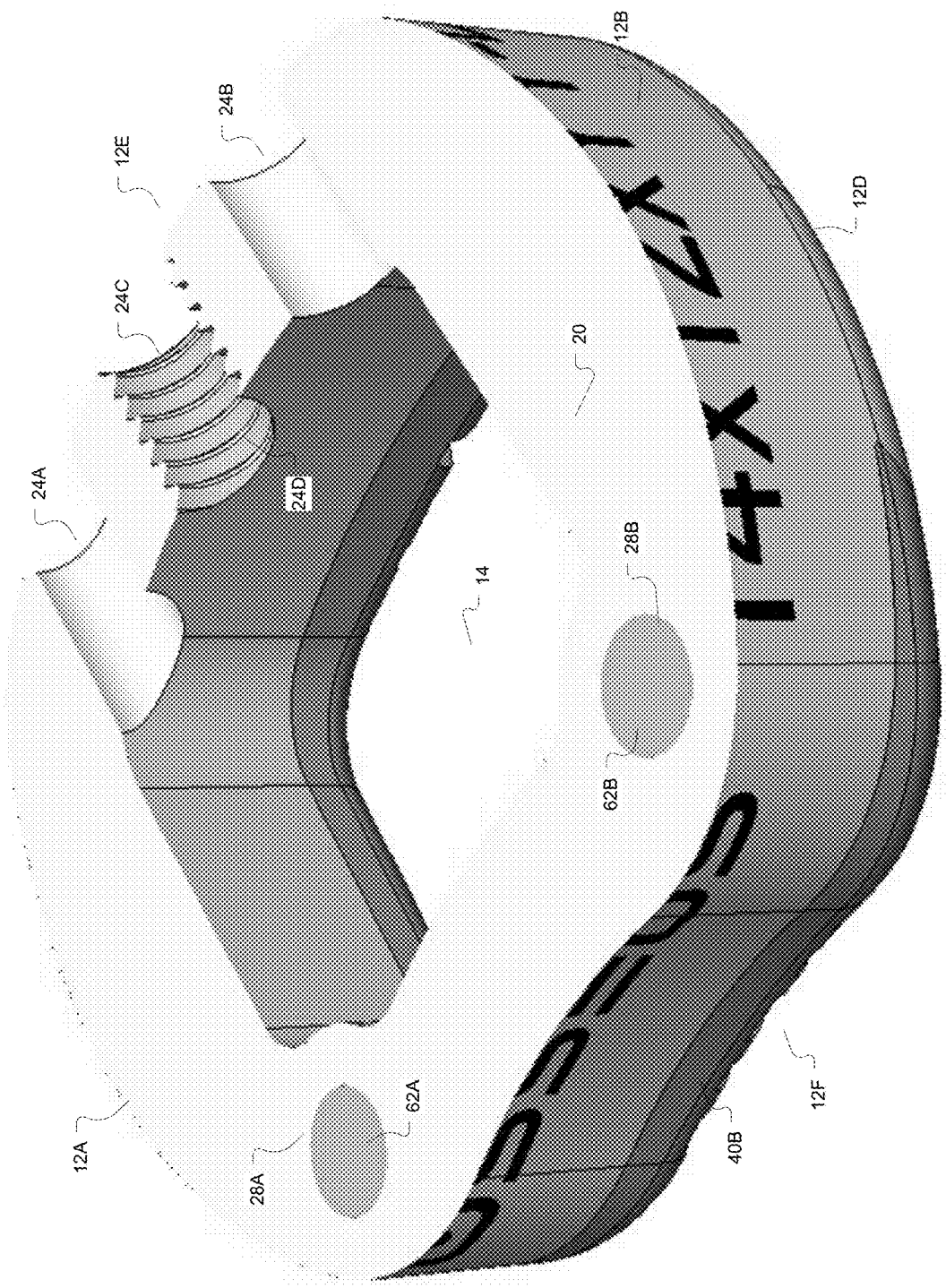
FIG. 1J is a simplified isometric cross sectional view of the composite interbody system shown in FIG. 1D taken along line BB according to various embodiments.

FIG. 1I is a simplified vertical cross sectional left side view of the composite interbody system 10 shown in FIG. 1C taken along line AA according to various embodiments. As shown in FIG. 1I, the main module 20 center fenestration 24C may have threads extending only its entire length. FIG. 1J is a simplified isometric cross sectional view of the composite interbody system 10 shown in FIG. 1D taken along line BB according to various embodiments. As shown in FIG. 1J, the linking modules 60A, 60B shafts 62A, 62B extend through the main module 20 fenestrations 28A, 28B. In an embodiment, the linking modules 60A, 60B shafts 62A, 62B inner diameter and the main module 20 fenestrations 28A, 28B diameter are about 0.5 to 3 mm and about 1.5 mm in an embodiment.

FIG. 2A is a simplified isometric view of a main module 20 of a composite interbody system 10 according to various embodiments. FIG. 2B is a simplified vertical cross sectional left side view of the main module 20 of a composite interbody system 10 shown in FIG. 2C taken along line CC according to various embodiments. As discussed and shown in FIGS. 2A and 2B, the main module 20 includes right and left shoulders 26A, 26B including undercuts 26C. The undercuts 26C may be sized to enable upper and lower modules 40A, 40B flanges or dovetails 46A, 46B to slidably and securely engage.

Figure 2C:
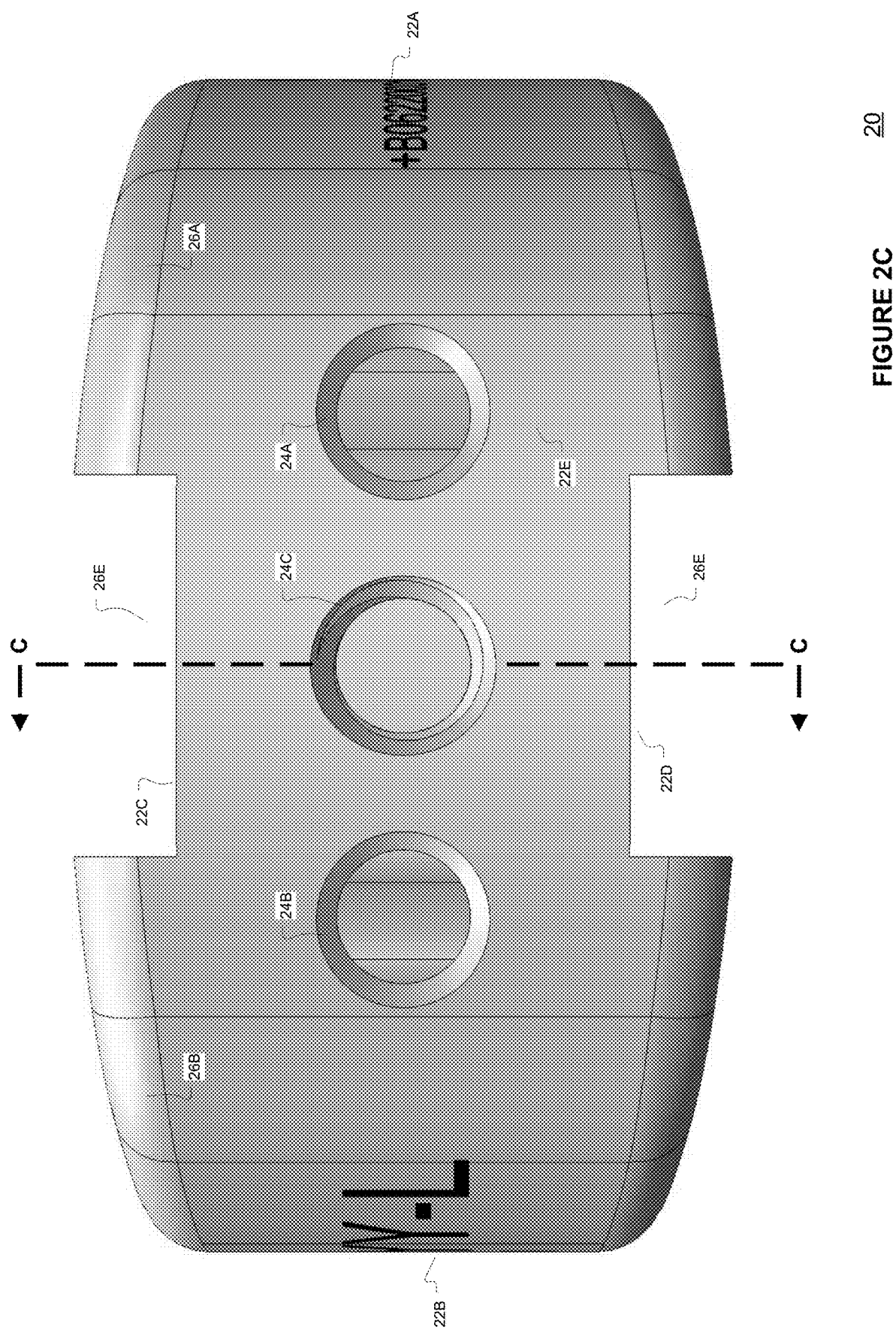
FIG. 2C is a simplified front view of a main module of a composite interbody system according to various embodiments.
Figure 2D:
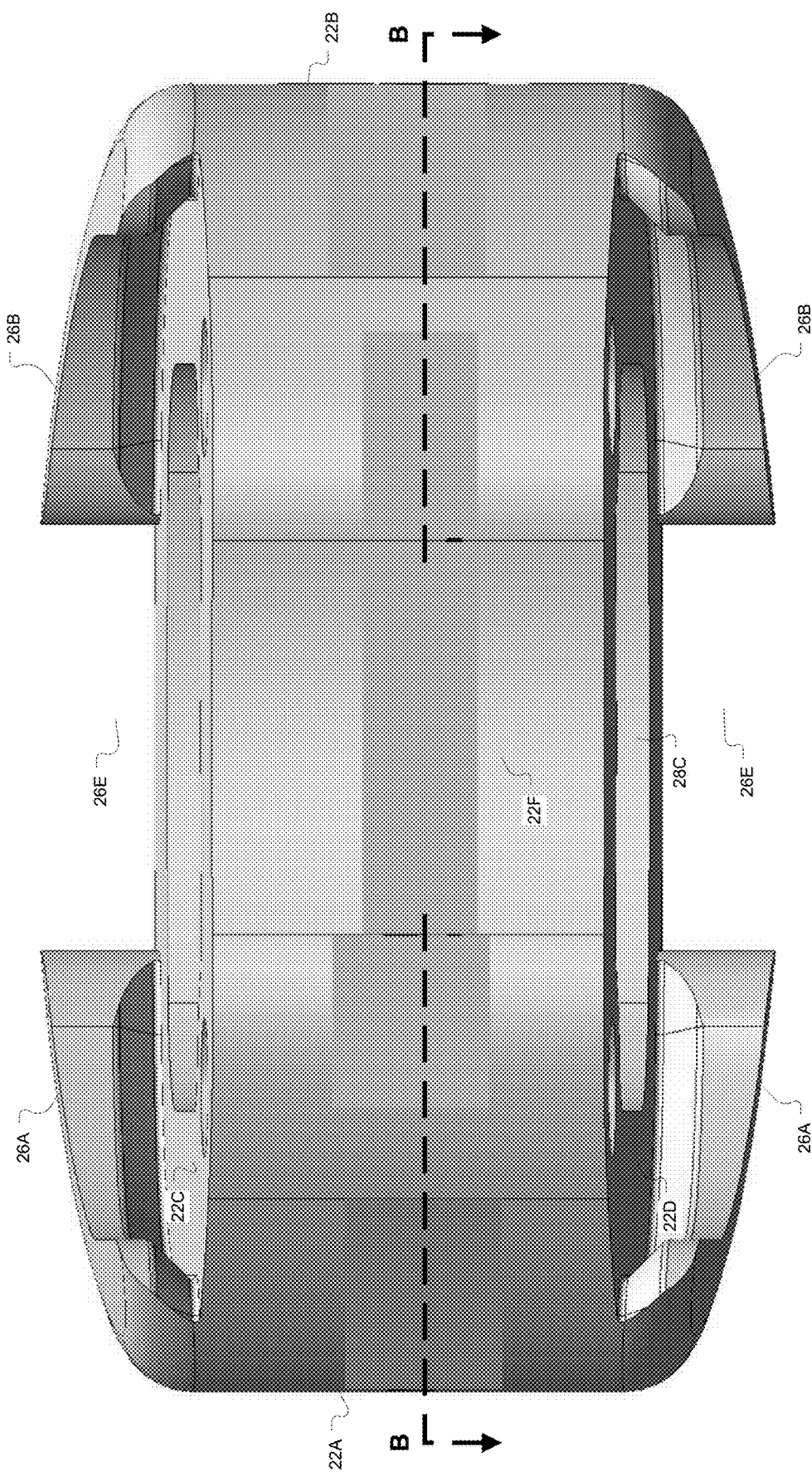
FIG. 2D is a simplified rear view of a main module of a composite interbody system according to various embodiments.

FIG. 2C is a simplified front view 22E of a main module 20 of a composite interbody system 10 according to various embodiments. As shown in FIG. 2C, the main body includes a front gap 26E formed by the right and left shoulders 26A, 26B where the gap 26E is sized to accommodate the upper and lower modules 40A, 40B front extensions 46C. FIG. 2D is a simplified rear view 22F of a main module of a composite interbody system according to various embodiments. FIG. 2D shown its top 22C may be symmetrical with its bottom 22D. As also shown in FIG. 2D, the main module 20 shoulders 26A, 26B may also form a an opening in the back 22F, top surface 22C to accommodate the upper and lower modules 40A, 40B back sides 42F.

Figure 2E:
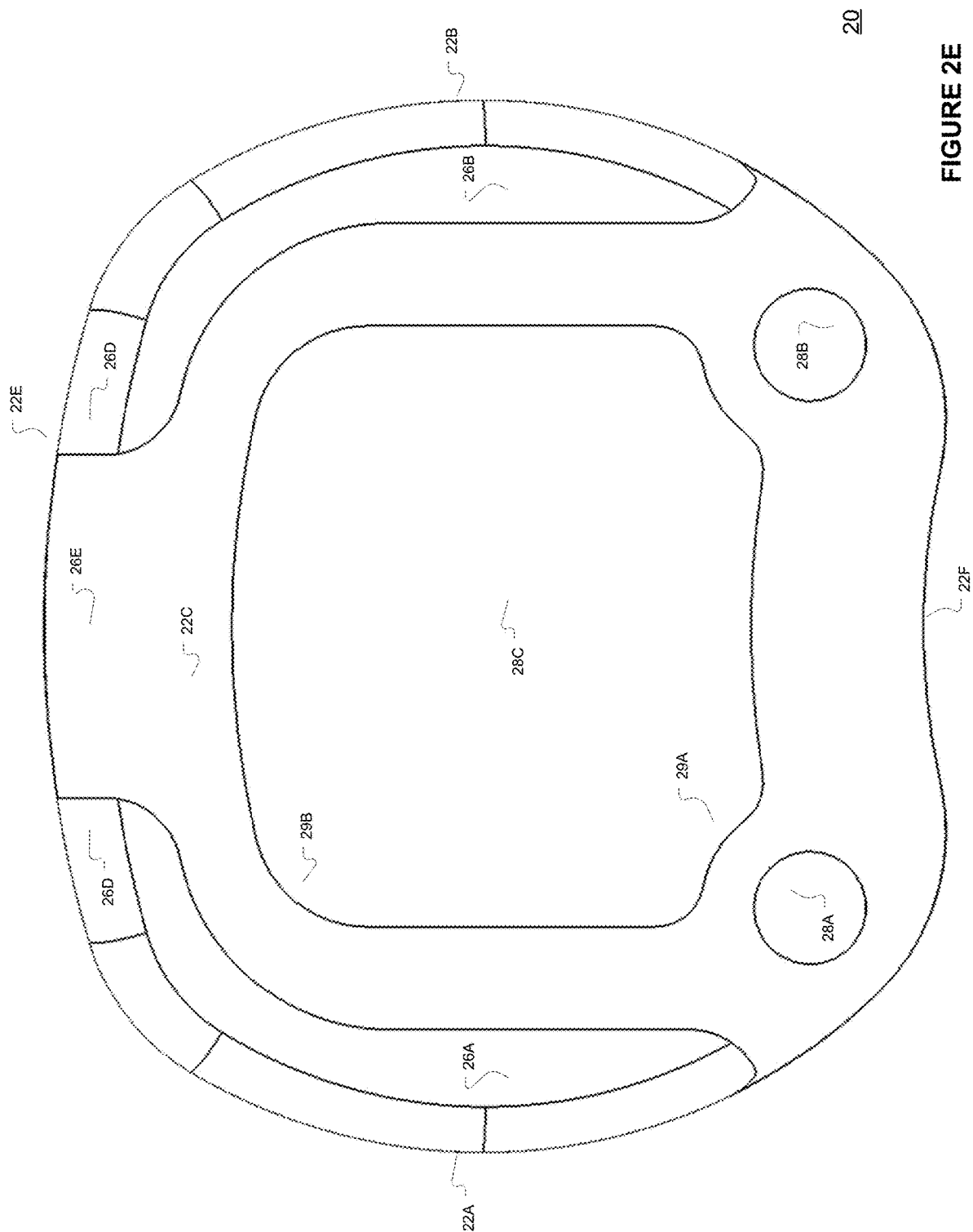
FIG. 2E is a simplified top view of a main module of a composite interbody system according to various embodiments.
Figure 2F:
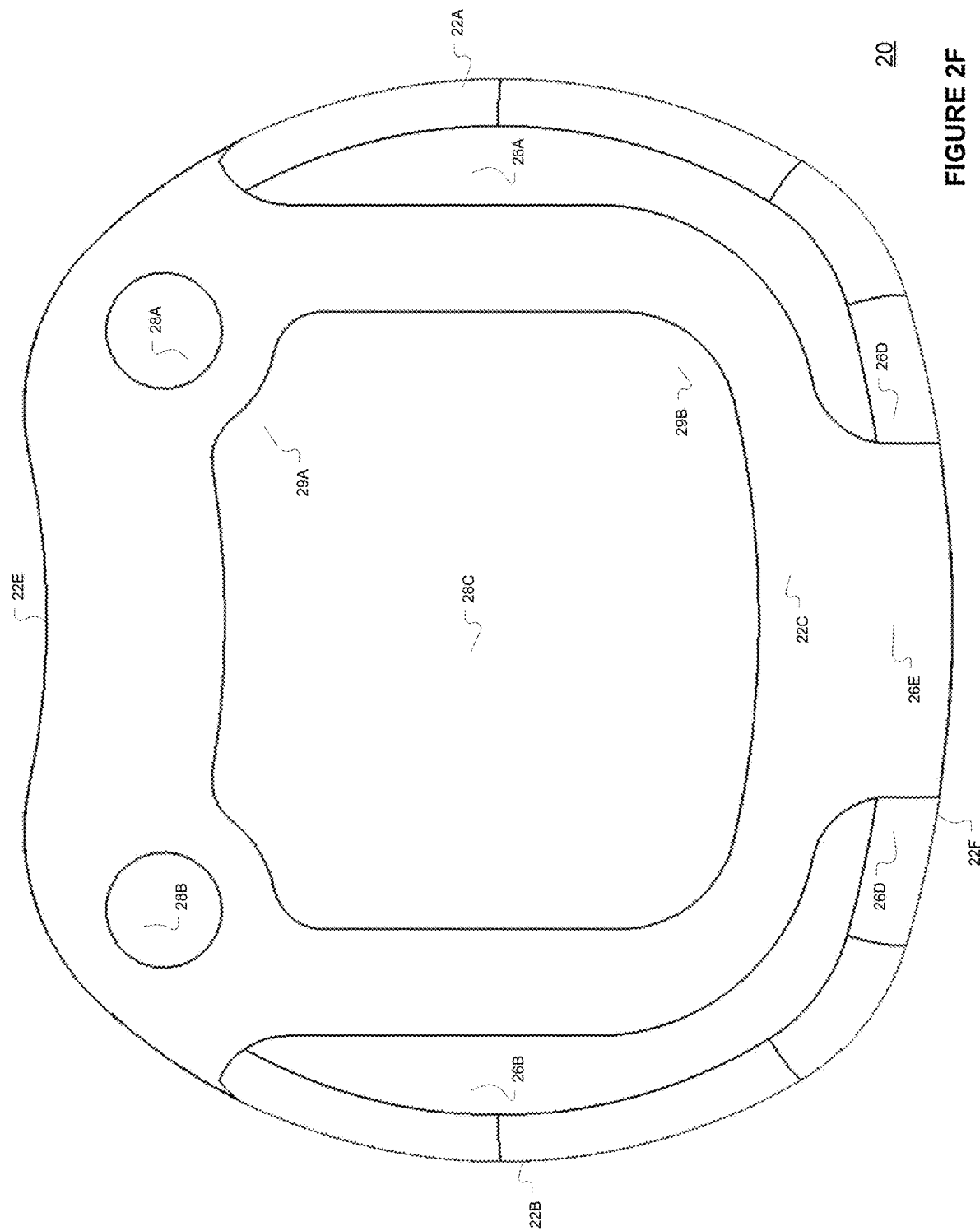
FIG. 2F is a simplified bottom view of a main module of a composite interbody system according to various embodiments.

FIG. 2E is a simplified top view 22C of a main module 20 of a composite interbody system 10 according to various embodiments. FIG. 2F is a simplified bottom view 22D of a main module 20 of a composite interbody system 10 according to various embodiments. As shown in FIGS. 2E and 2F, the main module 20 may include a central fenestration 28C that is similar or identical in size (length and width) as the upper and lower modules 40A, 40B central fenestrations 48C and form the composite interbody system 10 central fenestration 14. The composite interbody system 10 central fenestration 14 may be packed with oseoconductive material including autogenic bone to aid bony fusion between bony segments 72A-C where the composite interbody system 10 is intended to be deployed. As shown in FIG. 2E, the main module 20 central fenestration 28C may convexly curved back, left and right corners 29A and concavely curved front, left and right corners 29B.

Figure 2G:
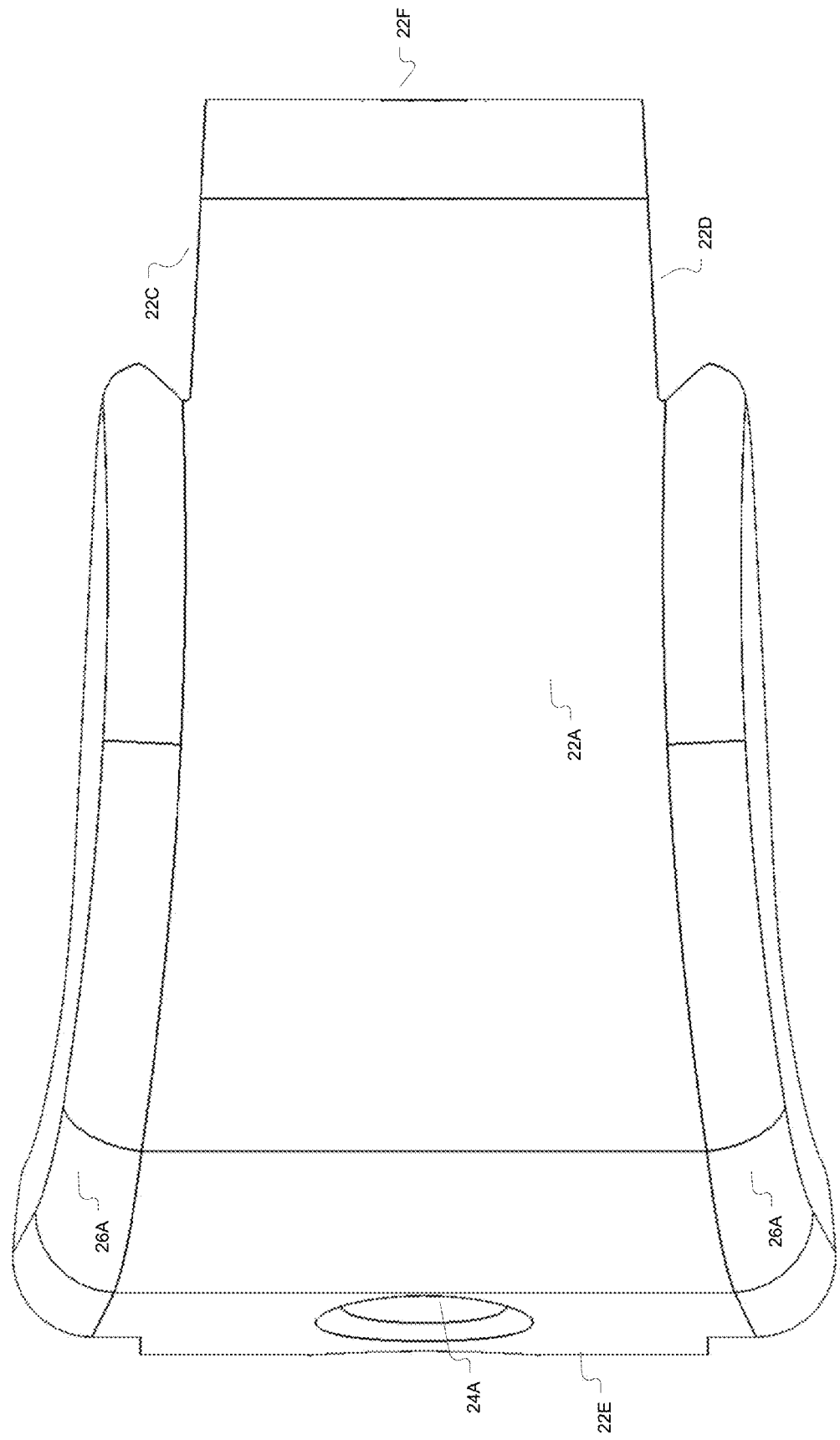
FIG. 2G is a simplified right side view of a main module of a composite interbody system according to various embodiments.
Figure 2H:
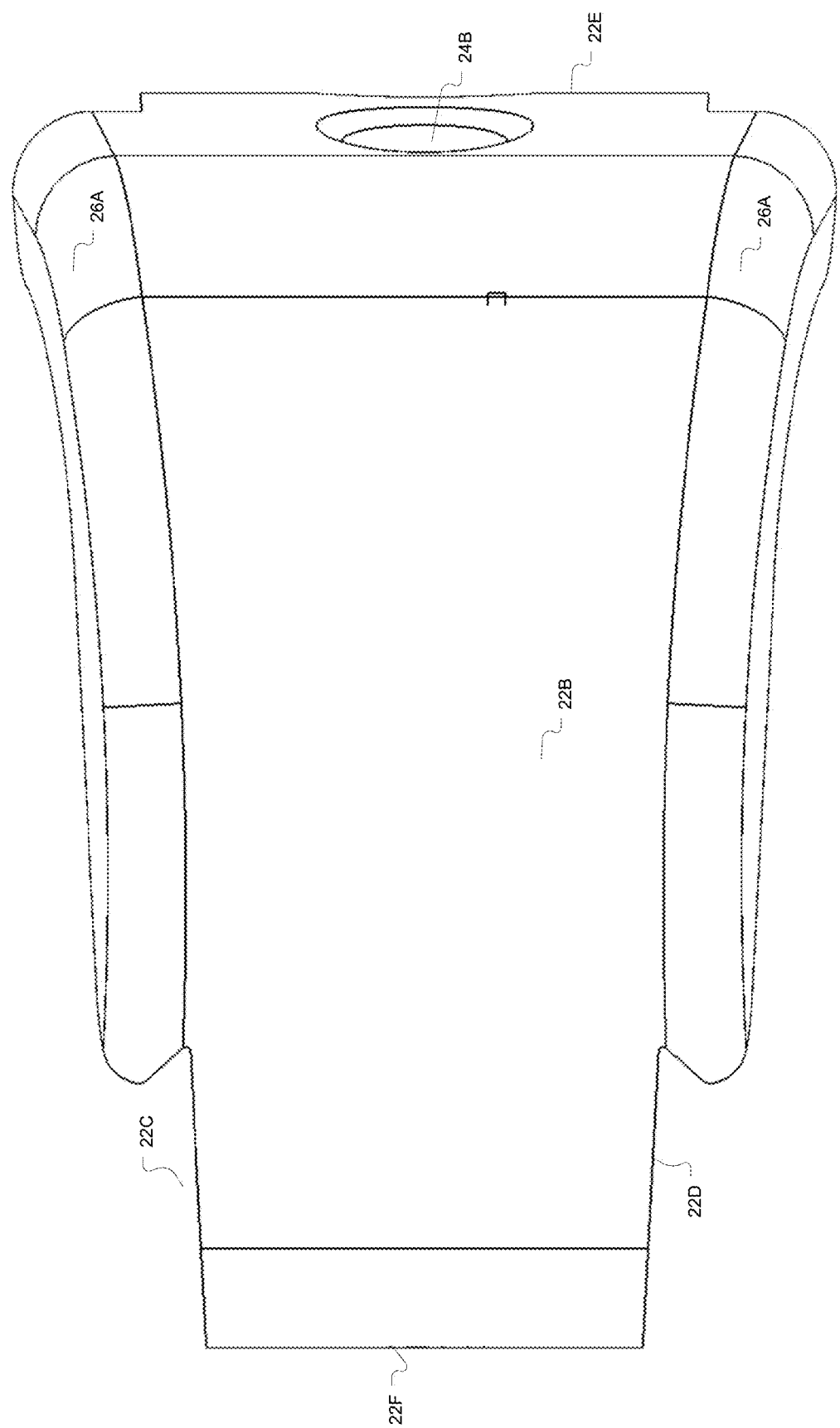
FIG. 2H is a simplified left side view of a main module of a composite interbody system according to various embodiments.

FIG. 2G is a simplified right side view and FIG. 2H is a simplified left side view of a main module 20 of a composite interbody system 10 according to various embodiments. As discussed, the composite interbody system 10 top 12C and bottom 12D and the main body 10 top 22C and bottom 22D may be sloped downwardly from its front side 22E to its back side 22F, about 6 degrees in an embodiment. The slope inclination from front 12E to back 12F may be selected or configured to match the bony segment surfaces including vertebra lordosis.

Figure 3A:
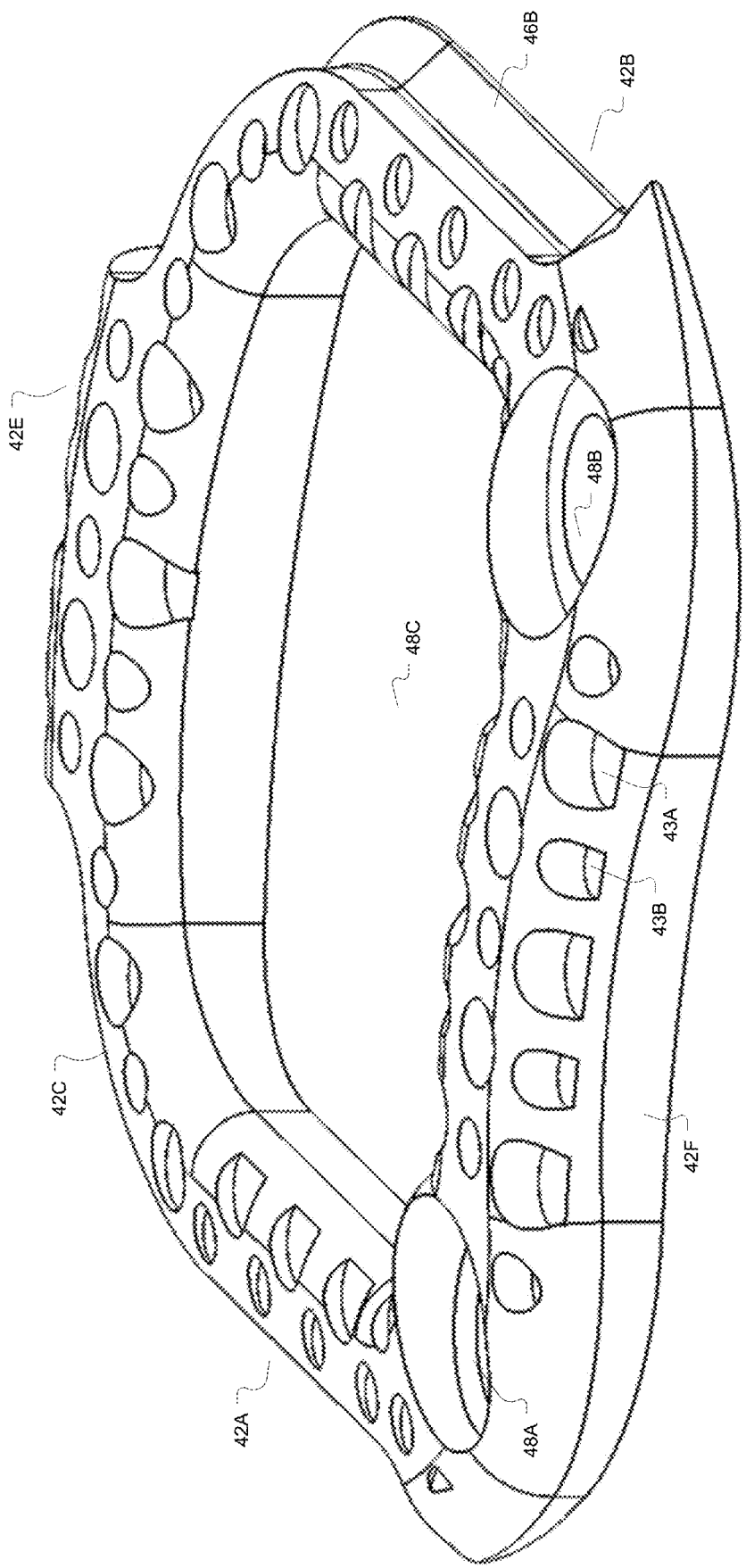
FIG. 3A is a simplified isometric view of an upper module of a composite interbody system according to various embodiments.
Figure 3D:
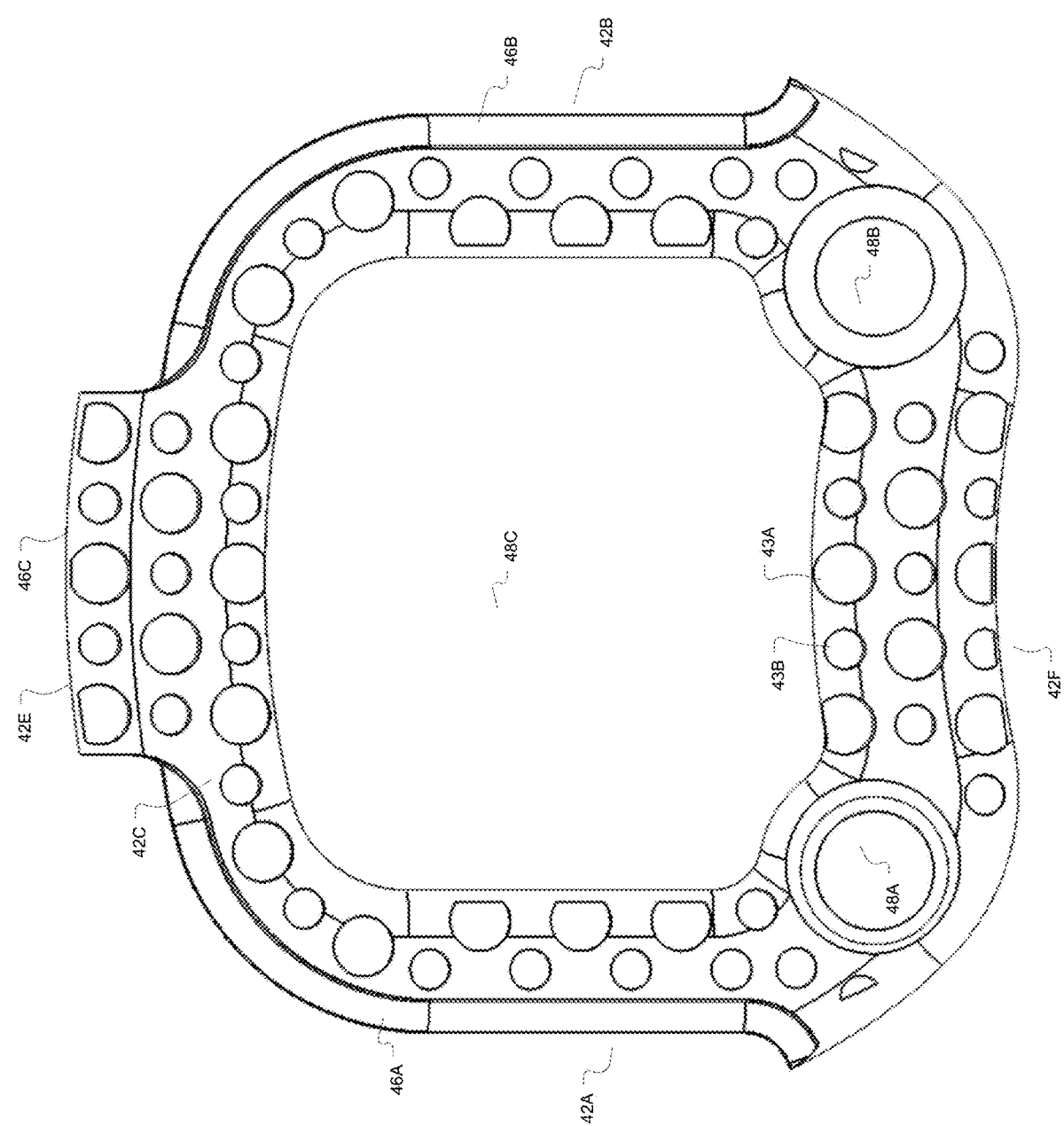
FIG. 3D is a simplified top view of an upper module of a composite interbody system according to various embodiments.
Figure 3E:
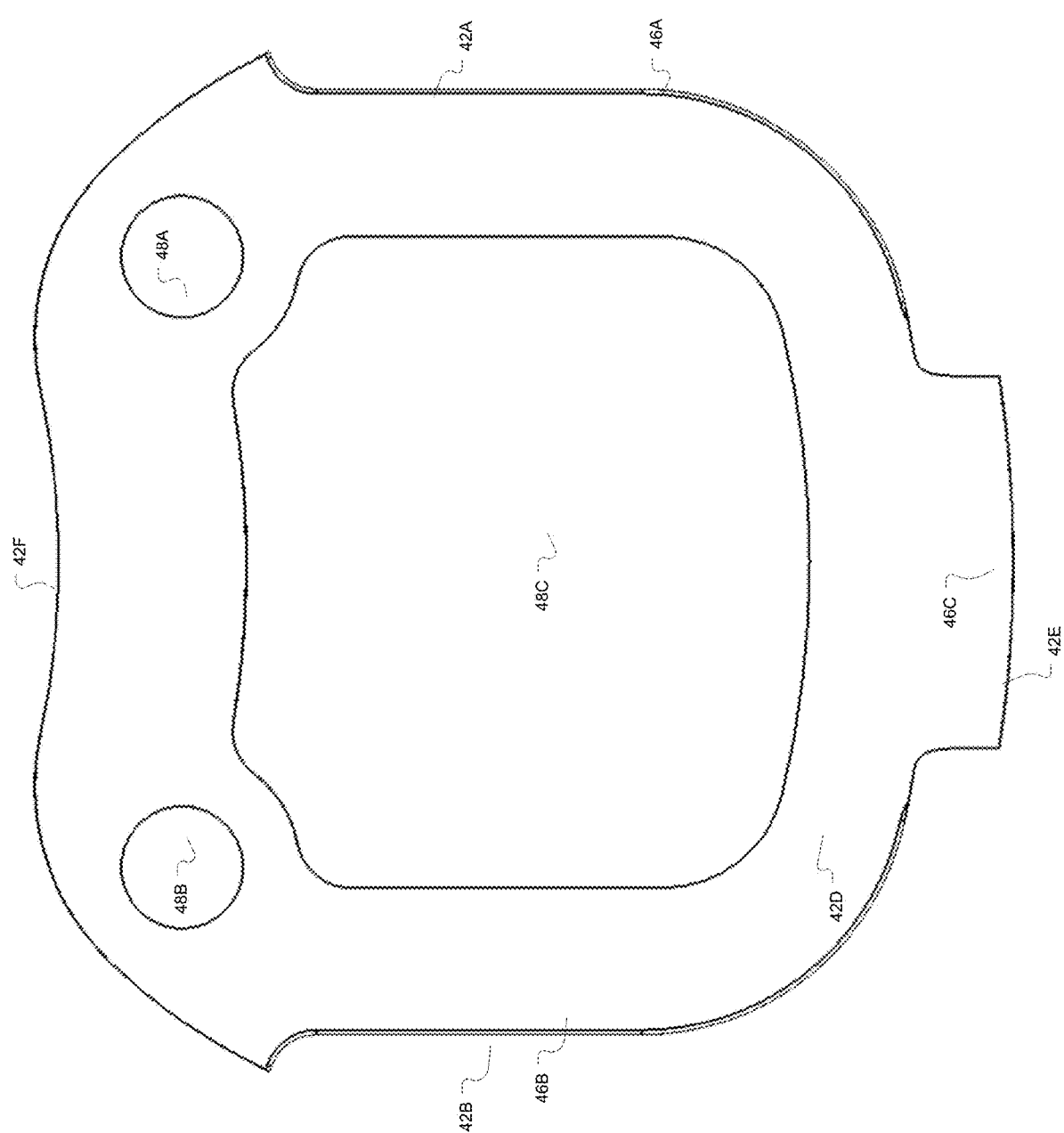
FIG. 3E is a simplified bottom view of an upper module of a composite interbody system according to various embodiments.

FIG. 3A is a simplified isometric view, FIG. 3B is a simplified front view, and FIG. 3C is a simplified rear view of an upper module 40A of a composite interbody system 10 according to various embodiments. FIG. 3D is a simplified top view and FIG. 3E is a simplified bottom view of an upper module 40A of a composite interbody system 10 according to various embodiments. FIG. 3F is a simplified right side view and FIG. 3G is a simplified left side view of an upper module 40A of a composite interbody system 10 according to various embodiments. As noted the lower module 40B may be symmetrical to the upper module 40A and thus FIGS. 3A to 3G may also be views of the lower module 40B in an embodiment. As shown in FIGS. 3A to 3G, the upper and lower modules 40A, 40B may include flanges or dovetails 46A, 46B on their respective right side 42A and left side 42B. The upper and lower modules 40A, 40B may include fenestrations 48A, 48B sized to accommodate the linking modules 60A, 60B shafts 62A, 62B while engaging their heads 64A or compressed tips 66A.

Figure 4B:
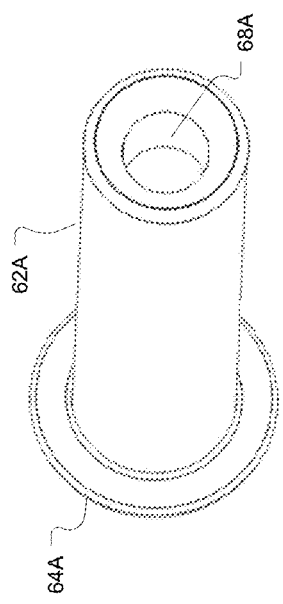
FIG. 4B is a simplified isometric bottom view of a lower module to upper module linking element of a composite interbody system according to various embodiments.
Figure 4C:
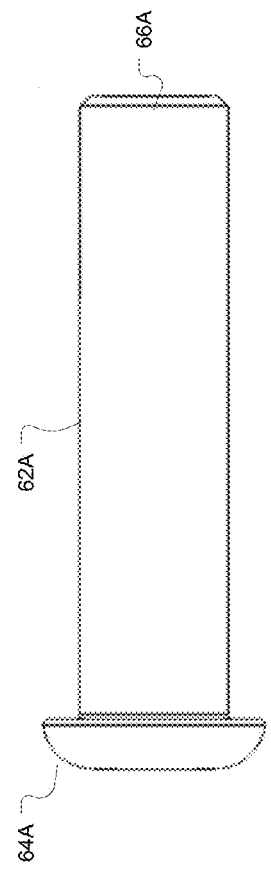
FIG. 4C is a simplified right side view of a lower module to upper module linking element of a composite interbody system according to various embodiments.
Figure 4A:
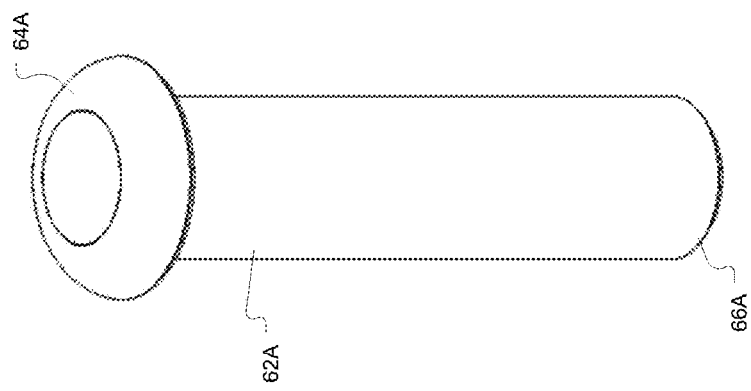
FIG. 4A is a simplified isometric front view of a lower module to upper module linking element of a composite interbody system according to various embodiments.

FIG. 4A is a simplified isometric front view, FIG. 4B is a simplified isometric bottom view, and FIG. 4C is a simplified right side view of a lower module to upper module linking element 60A of a composite interbody system 10 according to various embodiments. In an embodiment, the linking element 60A may be identical to the linking element 60B. As shown in FIGS. 4A to 4C, the linking module 60A may include a head 64A, elongated shaft 62A, and compressible tip 66A in an embodiment. In an embodiment, the head 64A diameter may be about 1 mm to 4 mm and about 2.25 mm when the shaft 62B diameter is about 1.5 mm.

The linking module 60A overall length (from head 64A to tip 66A) may vary as a function of the composite interbody system 10 height. In an embodiment, the linking modules 60A overall length may be about 0.7 mm less than the composite interbody system 10 maximum height. The linking module 60A tip 66A may be compressible via an opening 68A in the shaft 62A tip 66A to enable secure engagement with the upper module 40A right fenestration 48A. Similarly, the linking module 60B tip 66A may be compressible via an opening 68A in the shaft 62A tip 66A to enable secure engagement with the lower module 40A left fenestration 48B. The opening 68A may have a diameter of about 0.2 to 1.5 mm and about 0.8 mm when the shaft 62A diameter is about 1.5 mm. The opening 68A may have a length of about 0.5 to 3 mm and about 1.5 mm when the shaft 62A diameter is about 1.5 mm.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A composite interbody system for placement between two, adjacent bony mammalian regions, the system including:
    a main module formed of at least a first material and including a top side including a left shoulder and right shoulder and a bottom side including a left shoulder and right shoulder;
    a substantially planar upper module formed of at least a second material different from the at least a first material of the main module;
    a substantially planar lower module formed of at least the second material; and
    a plurality of linking elements, each fixably coupling the substantially planar upper module to the substantially planar lower module via a separate fenestration in the main module, each separate fenestration extending from a back section of the top side of the main module to a back section of the bottom side of the main module,
    wherein at least a portion of the substantially planar upper module is slidably coupled between the left shoulder and the right shoulder of the top side of the main module and at least a portion of the substantially planar lower module is slidably coupled between the left shoulder and the right shoulder of the bottom side of the main module and
    wherein the combination of the main module, the substantially planar upper module, and the substantially planar lower module together form the composite interbody system, the composite interbody system having a top side, a bottom side, a left side, a right side, a front side, and a back side and being configured and sized to be insertable, back side first between the two adjacent bony mammalian regions, the top side of the composite interbody system including surfaces configured to engage an upper bony region of the two adjacent bony mammalian regions and the bottom side of the composite interbody system including surfaces configured to engage a lower bony region of the two adjacent bony mammalian regions,
    wherein the substantially planar upper module and the substantially planar lower module each include fenestrations, each fenestration being aligned with a respective fenestration in the main module when the substantially planar upper module and the substantially planar lower module are slidably coupled to the main module top side and the main module bottom side, wherein each of the plurality of linking elements includes a first end configured to engage a fenestration of one of the substantially planar upper module and the substantially planar lower module and a second end configured to engage the fenestration of the other of the substantially planar upper module and the substantially planar lower module.

2. The composite interbody system of claim 1, wherein at least a portion of the left shoulder and the right shoulder of the top side of the main module are part of the surfaces of the top side of the composite interbody system configured to engage an upper bony region of the two adjacent bony mammalian regions and at least a portion of the left shoulder and the right shoulder of the bottom side of the main module are part of the surfaces of the bottom side of the composite interbody system configured to engage a lower bony region of the two adjacent bony mammalian regions.

3. The composite interbody system of claim 2, wherein the composite interbody system has a central fenestration extending from the top side to the bottom side of the composite interbody system which comprises more than 50% of a composite interbody system top side surface area and a composite interbody system bottom side surface area.

4. The composite interbody system of claim 1, wherein the substantially planar upper module forms a majority of a composite interbody system top side surface area and the substantially planar lower module forms a majority of a composite interbody system bottom side surface area.

5. The composite interbody system of claim 1, wherein the at least a portion of the substantially planar upper module is slidably coupled into a recess formed between the left shoulder and the right shoulder of the top side of the main module and the at least a portion of the substantially planar lower module is slidably coupled into a recess formed between the left shoulder and the right shoulder of the bottom side of the main module.

6. The composite interbody system of claim 5, wherein the left shoulder of the top side and the left shoulder of the bottom side of the main module each extend along a portion of the left side and a portion of the front side of the composite interbody system and wherein the right shoulder of the top side and the right shoulder of the bottom side of the main module each extend along a portion of the right side and a portion of the front side of the composite interbody system.

7. The composite interbody system of claim 6, wherein the left shoulder and the right shoulder of the top side of the main module each include undercuts that enable the substantially planar upper module to be slidably coupled into the recess formed between the left shoulder and the right shoulder of the top side of the main module and the left shoulder and the right shoulder of the bottom side of the main module each include undercuts that enable the substantially planar lower module to be slidably coupled into the recess formed between the left shoulder and the right shoulder of the bottom side of the main module.

8. The composite interbody system of claim 7, wherein the substantially planar upper module includes flanges on its left and right sides that are sized and configured to enable the substantially planar upper module to be slidably coupled to the main module top side left shoulder and right shoulder undercuts and the substantially planar lower module includes flanges on its left and right sides that are sized and configured to enable the substantially planar lower module to be slidably coupled to the main module bottom side left shoulder and right shoulder undercuts.

9. The composite interbody system of claim 1, wherein the second material is more osteoconductive than the first material.

10. The composite interbody system of claim 1, wherein the substantially planar upper module and the substantially planar lower module are formed of titanium and the main module is formed of a member of the polyaryletherketone family.

11. The composite interbody system of claim 1, wherein the substantially planar upper module and the substantially planar lower module each include a plurality of divots.

12. The composite interbody system of claim 1, wherein the substantially planar upper module and the substantially planar lower module each include a plurality of uniformly distributed divots.

13. The composite interbody system of claim 1, wherein the substantially planar upper module and the substantially planar lower module each include a plurality of uniformly distributed, differently sized divots.

14. The composite interbody system of claim 1, wherein the two adjacent bony mammalian regions are adjacent cervical vertebrae.

* * * * *